United States Patent
Fensome et al.

(10) Patent No.: US 7,192,956 B2
(45) Date of Patent: Mar. 20, 2007

(54) METHODS OF TREATING HORMONE-RELATED CONDITIONS USING CYCLOTHIOCARBAMATE DERIVATIVES

(75) Inventors: Andrew Fensome, Wayne, PA (US); Gary S. Grubb, Newtown Square, PA (US); Diane Deborah Harrison, Villanova, PA (US); Richard Craig Winneker, Penllyn, PA (US); Puwen Zhang, Audubon, PA (US); Jeffrey Curtis Kern, Gilbertsville, PA (US); Eugene Anthony Terefenko, Quakertown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/601,481

(22) Filed: Jun. 23, 2003

(65) Prior Publication Data

US 2004/0006060 A1    Jan. 8, 2004

Related U.S. Application Data

(60) Provisional application No. 60/391,871, filed on Jun. 25, 2002.

(51) Int. Cl.
A61K 31/535 (2006.01)
A61K 31/445 (2006.01)
A61K 31/135 (2006.01)

(52) U.S. Cl. .................... 514/230.5; 514/320; 514/648
(58) Field of Classification Search ............. 514/230.5, 514/320, 648
See application file for complete search history.

(56) References Cited

U.S. PATENT DOCUMENTS

| | | | |
|---|---|---|---|
| 6,258,802 B1 * | 7/2001 | Hodgen ........................ 514/169 |
| 6,355,648 B1 | 3/2002 | Fensome et al. | |
| 6,407,101 B1 | 6/2002 | Collins et al. | |
| 6,436,929 B1 | 8/2002 | Zhang et al. | |
| 6,509,334 B1 * | 1/2003 | Zhang et al. ............. 514/230.5 |
| 6,521,657 B2 | 2/2003 | Fensome et al. | |
| 6,583,145 B1 | 6/2003 | Fensome et al. | |
| 2002/0061875 A1 * | 5/2002 | Gast et al. ............. 514/212.08 |
| 2002/0169198 A1 | 11/2002 | Fensome et al. | |
| 2003/0083322 A1 | 5/2003 | Kraemer et al. | |
| 2003/0092711 A1 | 5/2003 | Zhang et al. | |

FOREIGN PATENT DOCUMENTS

| | | |
|---|---|---|
| GB | 2310660 A | 9/1997 |
| WO | WO-85/00519 A | 2/1985 |
| WO | PCT WO 00/66555 A1 | 11/2000 |
| WO | PCT WO 00/66570 A1 | 11/2000 |
| WO | WO-00/66571 A | 11/2000 |
| WO | WO 00/66581 A1 | 11/2000 |

OTHER PUBLICATIONS

Zhang et al., "Potent Nonsteroidal Progesterone Receptor Agonists: Synthesis and SAR study of 6-Aryl Benzoxazines", Bioorg. Med. Chem. Lett., 12: 787-790 (Mar. 11, 2002).

Fensome et al., "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonist Tanaproget", J. Med. Chem., 48: 5092-5095 (Aug. 11, 2005).

Zhang et al., "Novel 6-Aryl-1,3-dihydrobenzo[d][1,3]oxazine-2-thiones as Potent, Selective, and Orally Active Nonsteroidal Progesterone Receptor Agonists", Bioorg. Med. Chem. Lett., 13:1313-1316 (Apr. 7, 2003).

Winneker et al., "Nonsteroidal Progesterone Receptor Modulators: Structure Activity Relationships", Sem. Reprod. Med., 23(1): 46 (Feb. 2005).

* cited by examiner

*Primary Examiner*—Raymond J. Henley, III
(74) *Attorney, Agent, or Firm*—Howson and Howson; Arnold S. Milowsky

(57) ABSTRACT

The present invention provides methods of inducing contraception which includes delivering to a female a composition containing a compound of formula I or formula II, or tautomers thereof, in a regimen which involves delivering one or more of a selective estrogen receptor modulator, wherein formula I is:

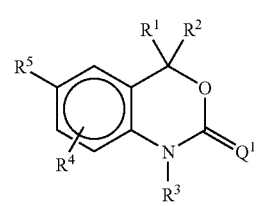

I and wherein $R^1$–$R^5$ and $Q^1$ are defined as described herein. Methods of providing hormone replacement therapy and for treating carcinomas, dysfunctional bleeding, uterine leiomyomata, endometriosis, and polycystic ovary syndrome is provided which includes delivering a compound of formula I and a selective estrogen receptor modulator are also described.

22 Claims, No Drawings

METHODS OF TREATING HORMONE-RELATED CONDITIONS USING CYCLOTHIOCARBAMATE DERIVATIVES

CROSS-REFERENCE TO RELATED APPLICATIONS

This is a non-provisional of U.S. Patent Application Ser. No. 60/391,871, filed Jun. 25, 2002.

BACKGROUND OF THE INVENTION

This invention relates generally to the treatment of hormone-related conditions using compositions containing small molecules.

A number of successful treatments have been found in the treatment of hormone related conditions and include the delivery of natural and synthetic hormones. Specifically, estrogen has been utilized for its positive effects including the maintenance of bone density, central nervous system (CNS) function, and the protection of organ systems from the effects of aging. However, the delivery of estrogen also has important disadvantages including an increase in the risk of cancers.

There exists a continued need in the art for alternative methods of alleviating the symptoms and/or resolving a variety of hormone related conditions.

SUMMARY OF THE INVENTION

In one aspect, a method of inducing contraception is provided which includes delivering a compound of formula I or formula II and a selective estrogen receptor modulator.

In another aspect, a method of providing hormone replacement therapy is provided which includes delivering a compound of formula I or formula II and a selective estrogen receptor modulator.

In a further aspect, methods of treating carcinomas, dysfunctional bleeding, uterine leiomyomata, endometriosis, and polycystic ovary syndrome is provided which includes delivering a compound of formula I or formula II and a selective estrogen receptor modulator.

Other aspects and advantages of the present invention are described further in the following detailed description of the preferred embodiments thereof.

DETAILED DESCRIPTION OF THE INVENTION

The present invention provides methods of treating hormone related conditions including delivering to a mammal a composition comprising a compound of formula I or formula II in a regimen which includes delivering a pharmaceutically effective amount of one or more of a selective estrogen receptor modulator to the mammal.

Preferably, the mammalian patient treated according to the present invention is a human, and more preferably a female. When used for inducing contraception, the mammalian patient is a female of child-bearing age. Further, when used for providing hormone replacement therapy, the mammalian patient is preferably a pre-menopausal, menopausal, or post-menopausal female.

The term "selective estrogen receptor modulator" or "SERM" is meant to describe a compound that exhibits activity as an agonist or antagonist of an estrogen receptor in a tissue-dependent manner. SERMs can act as estrogen receptor agonists in some tissues and as antagonists in other tissue types. The term SERMs can also be interchanged with the term "anti-estrogen".

The term estrogen is mean to describe any estrogenic agent. Preferably, the estrogenic agent is a conjugated equine estrogen.

A number of hormone-related conditions can be treated according to the methods of the present invention. Preferably, estrogen-related conditions are treated using the compositions of the present invention. Such estrogen related conditions can include, without limitation, the induction of contraception, providing hormone replacement therapy, the treatment of obesity, carcinomas, osteoporosis, endometriosis, menopausal syndromes (including perimenopausal, menopausal, or postmenopausal syndromes), hair loss (alopecia), diabetes, Alzheimer's Disease, urinary incontinence, arthritis, gastrointestinal (GI) tract conditions, acne, cataracts, hirsutism, polycystic ovary syndrome, uterine leiomyomata, multiple myeloma, dysfunctional bleeding, lymphoma, dysmennorhea, and the stimulation of food intake. Examples of carcinomas that can be treated according to the present invention include breast, prostate, colon, lung, ovarian, melanoma, central nervous system (CNS), cervical, uterine, endometrial, and renal carcinomas.

The present invention provides methods of inducing contraception including the step of delivering to a female of child-bearing age a composition comprising a compound of formula I or formula II in a regimen which involves delivering a pharmaceutically effective amount of one or more of a selective estrogen receptor modulator to the female.

Also provided are methods for providing hormone replacement therapy including the step of delivering to a female a composition comprising a compound of formula I or formula II in a regimen which involves delivering a pharmaceutically effective amount of one or more of a selective estrogen receptor modulator to the female. Such therapy can be performed during menopause, or pre- or post-menopause.

The present invention further provides methods for treating carcinomas including the step of delivering to a mammal in need thereof a composition comprising a compound of formula I or formula II in a regimen which involves delivering a pharmaceutically effective amount of one or more of a selective estrogen receptor modulator to the mammal.

Additionally provided are methods for treating dysfunctional bleeding, uterine leiomyomata, endometriosis, or polycystic ovary syndrome, including the step of delivering to a female in need thereof a composition comprising a compound of formula I or formula II in a regimen which involves delivering a pharmaceutically effective amount of one or more of a selective estrogen receptor modulator to the female.

I. Compositions Useful in the Methods of the Invention

In one embodiment, the methods of the present invention include the delivery of compounds of formula I, the preparation of which is described in International Patent Publication No. WO 00/66570, and hereby incorporated by reference. Suitably, these compounds are progesterone-receptor (PR) modulators, which, when used in the methods of the invention, are delivered as a PR agonist. The compounds of formula I have the structure:

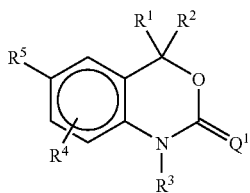

I wherein:

$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $COR^A$, and $NR^BCOR^A$;

or $R^1$ and $R^2$ are fused to form a ring selected from the group consisting of a), b) and c), wherein said ring is optionally substituted by from 1 to 3 substituents selected from the group consisting of H and $C_1$ to $C_3$ alkyl;

a) a carbon-based 3 to 8 membered saturated spirocyclic ring;

b) a carbon-based 3 to 8 membered spirocyclic ring having one or more carbon-carbon double bonds; and c) a 3 to 8 membered spirocyclic ring having in its backbone one to three heteroatoms selected from the group consisting of O, S and N;

$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl;

$R^B$ is selected from the group consisting of H, $C_1$ to $C_3$ alkyl, and substituted $C_1$ to $C_3$ alkyl;

$R^3$ is selected from the group consisting of H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, and $COR^C$;

$R^C$ is selected from the group consisting of H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, and substituted $C_1$ to $C_4$ aminoalkyl;

$R^4$ is selected from the group consisting of H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is selected from the group consisting of (i) and (ii):

(i) a substituted benzene ring having the structure:

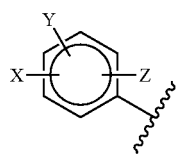

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $COR^D$, $OCOR^D$, and $NR^ECOR^D$;

$R^D$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^E$ is selected from the group consisting of H, $C_1$ to $C_3$ alkyl, and substituted $C_1$ to $C_3$ alkyl;

Y and Z are independent substituents selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl; and b) a five or six membered carbon-based heterocyclic ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $C_1$ to $C_3$ thioalkyl, substituted $C_1$ to $C_3$ thioalkyl, $COR^F$, and $NR^GCOR^F$;

$R^F$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, $C_1$ to $C_3$ alkyl, and $C_1$ to $C_4CO_2$alkyl;

$Q^1$ is selected from the group consisting of S, $NR^7$, and $CR^8R^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $SO_2CF_3$, $OR^{11}$, and $NR^{11}R^{12}$;

$R^8$ and $R^9$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $NO_2$, CN, and $CO_2R^{10}$;

$R^{10}$ is selected from the group consisting of $C_1$ to $C_3$ alkyl and substituted $C_1$ to $C_3$ alkyl;

or $CR^8R^9$ comprise a six membered ring having the structure:

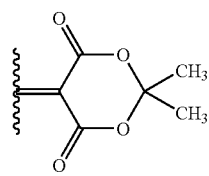

$R^{11}$ and $R^{12}$ are independently selected from the group consisting of H, $C_1$ to $C_6$ alkyl, substituted $C_1$ to $C_6$ alkyl, aryl, substituted aryl, carbon-based heterocyclic ring having in its backbone 1 to 3 heteroatoms, substituted carbon-based heterocyclic ring having in its backbone 1 to 3 heteroatoms, acyl, substituted acyl, sulfonyl, and substituted sulfonyl;

or a pharmaceutically acceptable salt, tautomer, metabolite, or prodrug thereof.

In a further embodiment, the compound is of formula I:

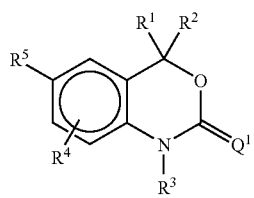

wherein:

$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, and substituted carbon-based heterocyclic ring having in its backbone 1 to 3 heteroatoms;

or $R^1$ and $R^2$ are fused to form a ring selected from the group consisting of a), b) and c), wherein said ring is optionally substituted by from 1 to 3 substituents selected from the group consisting of H and $C_1$ to $C_3$ alkyl;

a) a carbon-based 3 to 8 membered saturated spirocyclic ring;

b) a carbon-based 3 to 8 membered spirocyclic ring having one or more carbon-carbon double bonds; and c) a 3 to 8 membered spirocyclic ring having in its backbone one to three heteroatoms selected from the group consisting of O, S and N;

$R^3$ is H;

$R^4$ is selected from the group consisting of H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is selected from the group consisting of (i) and (ii):

(i) a substituted benzene ring having the structure:

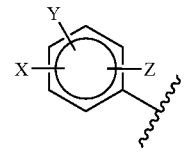

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $COR^D$, $OCOR^D$, and $NR^ECOR^D$;

$R^D$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^E$ is selected from the group consisting of H, $C_1$ to $C_3$ alkyl, and substituted $C_1$ to $C_3$ alkyl;

Y and Z are independent substituents selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl; and b) a five or six membered carbon-based heterocyclic ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $C_1$ to $C_3$ thioalkyl, substituted $C_1$ to $C_3$ thioalkyl, $COR^F$, and $NR^GCOR^F$;

$R^F$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, $C_1$ to $C_3$ alkyl, and $C_1$ to $C_4$ $CO_2$alkyl;

$Q^1$ is S;

or a pharmaceutically acceptable salt, tautomer, metabolite, or prodrug thereof.

In yet another embodiment, the compound is selected from the group consisting of 6-(3-Chlorophenyl)-4,4-dimethyl-1,4-dihydro-benzo[d][1,3]oxazin-2-thione, 4-(4,4-Dimethyl-2-thioxo-1,4-dihydro-2H-benzo[d][1,3]oxazin-6-yl)-thiophene-2-carbonitrile, 3-(4,4-Dimethyl-2-thioxo-1,4-dihydro-2H-benzo[d][1,3]oxazin-6-yl)-5-fluorobenzonitrile, 3-(4,4-Dimethyl-2-thioxo-1,4-dihydro-2H-benzo[d][1,3]oxazin-6-yl)-benzonitrile, 6-(3-fluorophenyl)-4-methyl-1,4-dihydro-2H-3,1-benzoxazine-2-thione, 5-(4,4-Dimethyl-2- thioxo-1,4-dihydro-2H-3,1-benzoxazin-6-yl)-4-methylthiophene-2-carbonitrile, tert-Butyl 2-cyano-5-(4,4-dimethyl-2-thioxo-1,4-dihydro-2H-3,1-benzoxazin-6-yl)-1H-pyrrole-1-carboxylate, 5-(4,4-Dimethyl-2-thioxo-1,4-dihydro-2H-3,1-benzoxazin-6-yl)-1H-pyrrole-2-carbonitrile, [6-(4,4-dimethyl-2-thioxo-1,4-dihydro-2H-3,1-benzoxazin-6-yl)-pyridin-2-yl]acetonitrile, 5-(4,4-Dimethyl-2-thioxo-1,4-dihydro-2H-3,1-benzoxazin-6-yl)-1-methyl-1H-pyrrole-2-carbonitrile, 5-(4,4-dimethyl-2-thioxo-1,4-dihydro-2H-3,1-benzoxazin-6-yl)-1H-pyrrole-2-carbothiamide, 5-(4,4-Dimethyl-2-thioxo-1,4-dihydro-2H-benzo[d][1,3]oxazin-6-yl)thiophene-3-carbonitrile, 5-(4,4-dimethyl-2-thioxo-1,4-dihydro-2H-3,1-benzoxazin-6-yl)-1-ethyl-1H-pyrrole-2-carbonitrile, 4-(1,2-Dihydro-2-thioxospiro[4H-3,1-benzoxazin-4,1-cyclohexan]-6-yl)-2-thiophenecarbonitrile, 5-(4,4-Dimethyl-2-thioxo-1,4-dihydro-2H-3,1-benzoxazin-6-yl)-2-fluorobenzonitrile, 6-(5-Bromopyridin-3-yl)-4,4-dimethyl-1,4-dihydro-2H-3,1-benzoxazine-2-thione, 6-(3-Chloro-5-fluorophenyl)-4,4-dimethyl-1,4-dihydro-2H-3,1-benzoxazine-2-thione, 6-(3-Bromo-5-methylphenyl)-4,4-dimethyl-1,4-dihydro-2H-3,1-benzoxazine-2-thione, 6-(3-Bromo-5-trifluoromethoxyphenyl)-4,4-dimethyl-1,4-dihydro-2H-3,1-benzoxazine-2-thione, 3-(1,2-Dihydro-2-thioxospiro[4H-3,1-benzoxazine-4,1-cyclohexan]-6-yl)-5-fluorobenzonitrile, 3-(4,4-Dimethyl-2-thioxo-1,4-dihydro-2H-3,1-benzoxazin-6-yl)-5-methylbenzonitrile, 6-(3,5-Dichlorophenyl)-4,4-dimethyl-1,4-dihydro-2H-3,1-benzoxazine-2-thione, 5-(4,4-Dimethyl-1,2-thioxo-1,4-dihydro-2H-3,1-benzoxazin-6-yl) isophthalonitrile, 5-(4,4-Dimethyl-2-thioxo-1,4-dihydro-2H-3,1-benzoxazin-6-yl)-2-furonitrile, 4,4-Diethyl-6-(3-nitrophenyl)-1,4-dihydro-2H-3,1-benzoxazine-2-thione, 6-(3-Chlorophenyl)-4-methyl-4-phenyl-1,4-dihydro-2H-3,1-benzoxazine-2-thione, 4-Allyl-6-(3-chlorophenyl)-4-methyl-1,4-dihydro-2H-3,1-benzoxazine-2-thione, 3-Chloro-5-(4,4-dimethyl-2-thioxo-1,4-dihydro-2H-3,1-benzoxazin-6-yl)benzonitrile, 6-(3,5-Difluorophenyl)-4,4-dimethyl-1,4-dihydro-2H-3,1-benzoxazine-2-thione, 6-(3-Fluoro-5-methoxyphenyl)-4,4-dimethyl-1,4-dihydro-2H-3,1-benzoxazine-2-thione, 3-(4,4-Dimethyl-2-thioxo-1,4-dihydro-2H-3,1-benzoxazin-6-yl)-5-methoxybenzonitrile, 6-(3-Fluorophenyl)-4,4-dimethyl-1,4-dihydro-2H-3,1-benzoxazine-2-thione, 6-[3-Fluoro-5-(trifluoromethyl)phenyl]-4,4-dimethyl-1,4-dihydro-2H-3,1-benzoxazine-2-thione, 6-(2-Fluorophenyl)-4,4-dimethyl-1,4-dihydro-2H-3,1-benzoxazine-2-thione, 6-(3,4-Difluorophenyl)-4,4-dimethyl-1,4-dihydro-2H-3,1-benzoxazine-2-thione, 6-(4-Fluorophenyl)-4,4-dimethyl-1,4-dihydro-2H-3,1-benzoxazine-2-thione, 3-(4,4-Dimethyl-2-thioxo-1,4-dihydro-2H-3,1-benzoxazin-6-yl)-4-fluorobenzonitrile, 6-(2,3-Difluorophenyl)-4,4-dimethyl-1,4-dihydro-2H-3,1-benzoxazine-2-thione, 3-(8-Bromo-4,4-dimethyl-2-thioxo-1,4-dihydro-2H-3,1-benzoxazin-6-yl)-5-fluorobenzonitrile, 4,4-Dimethyl-6-(3-nitrophenyl)-1,4-dihydro-2H-3,1-benzoxazine-2-thione, 6-(3-Chlorophenyl)-4,4-diethyl-1,4-dihydro-2H-3,1-benzoxazine-2-thione, 6-(3-Methoxyphenyl)-4,4-dimethyl-1,4-dihydro-2H-3,1-benzoxazine-2-thione, 6-(2-Chlorophenyl)-4,4-dimethyl-1,4-dihydro-2H-3,1-benzoxazine-2-thione, 4-Benzyl-6-(3-chlorophenyl)-4-methyl-1,4-dihydro-2H-3,1-benzoxazine-2-thione, 6-(3-Bromo-5-fluorophenyl)-4,4-dimethyl-1,4-dihydro-2H-3,1-benzoxazine-2-thione, 5-(4,4-Dimethyl-2-thioxo-1,4-dihydro-2H-3,1-benzoxazin-6-yl)thiophene-2-carbonitrile, 3-Fluoro-5-(8-fluoro-4,4-dimethyl-2-thioxo-1,4-dihydro-2H-3,1-benzoxazin-6-yl)benzonitrile, 3-(1,2-Dihydro-2-thioxospiro[4H-3,1-benzoxazine-4,1-cyclohexan]-6-yl)benzonitrile, 5-(1,2-Dihydro-2-thioxospiro[4H-3,1-benzoxazine-4,1-cyclohexan]-6-yl)-4-methyl-2-thiophenecarbonitrile, 5-(1,2-Dihydro-2-thioxospiro[4H-3,1-benzoxazine-4,1-cyclohexan]-6-yl)-2-thiophenecarbonitrile, 6-(3-Chloro-4-fluorophenyl)-4,4-dimethyl-1,4-dihydro-2H-3,1-benzoxazine-2-thione, 5-(4,4-Dimethyl-2-thioxo-1,4-dihydro-2H-3,1-benzoxazin-6-yl)-4-propylthiophene-2-carbonitrile, 4-(4,4-Dimethyl-2-thioxo-1,4-dihydro-2H-3,1-benzoxazin-6-yl)-2-furonitrile, 4-Butyl-5-(4,4-dimethyl-2-thioxo-1,4-dihydro-2H-3,1-benzoxazin-6-yl)thiophene-2-carbonitrile, 6-(3-Bromophenyl)-4,4-dimethyl-1,4-dihydro-2H-3,1-benzoxazine-2-thione, and 2-(4,4-Dimethyl-2-thioxo-1,4-dihydro-2H-3,1-benzoxazin-6-yl)thiophene-3-carbonitrile, or a pharmaceutically acceptable salt, tautomer, metabolite, or prodrug thereof. Preferably, the compound is 5-(4,4-Dimethyl-2-thioxo-1,4-dihydro-2H-3,1-benzoxazin-6-yl)-1-methyl-1H-pyrrole-2-carbonitrile.

In another aspect, compounds of formula II can be utilized, where formula II is:

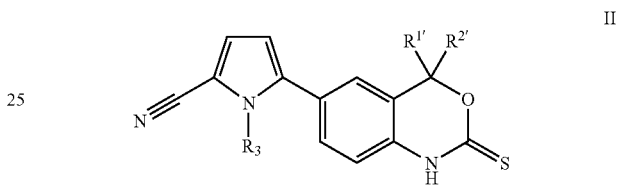

wherein $R^{1'}$ is selected from the group methyl, ethyl, trifluoromethyl; $R^{2'}$ is selected from the group methyl, ethyl, trifluoromethyl; or $R^{1'}$ and $R^{2'}$ are joined to form a spirocyclic ring containing 3 to 7 carbon atoms; and $R^{3'}$ is selected from the group $C_1$ to $C_4$ alkyl, and tautomers, prodrugs, metabolites, or pharmaceutically acceptable salts thereof.

Particularly desirable compounds of formula II include, 5-(4-ethyl-4-methyl-2-thioxo-1,4-dihydro-2H-3,1-benzoxazin-6-yl)-1-methyl-1H-pyrrole-2-carbonitrile, 5-(4,4-diethyl-2-thioxo-1,4-dihydro-2H-3,1-benzoxazin-6-yl)-1-methyl-1H-pyrrole-2-carbonitrile, 1-methyl-5-(2-thioxo-1,2-dihydrospiro[3,1-benzoxazine-4,1'-cyclobutan]-6-yl)-1H-pyrrole-2-carbonitrile, 1-methyl-5-(2-thioxo-1,2-dihydrospiro[3,1-benzoxazine-4,1'-cyclohexan]-6-yl)-1H-pyrrole-2-carbonitrile, 1-methyl-5-(2-thioxo-1,2-dihydrospiro[3,1-benzoxazine-4,1'-cyclopentan]-6-yl)-1H-pyrrole-2-carbonitrile, 1-methyl-5-[2-thioxo-4,4-bis(trifluoromethyl)-1,4-dihydro-2H-3,1-benzoxazine-6-yl]-1H-pyrrole-2-carbonitrile, prodrugs, metabolites, or pharmaceutically acceptable salts thereof.

The compounds utilized according to the present invention can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups having about 1 to about 8 carbon atoms, and preferably about 1 to about 6 carbon atoms. The term "alkenyl" is used herein to refer to both straight- and branched-chain alkyl groups having one or more carbon-carbon double bonds and containing about 2 to about 8 carbon atoms. Preferably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. Preferably, the term alkynyl refers to an alkyl group having 1 or 2 carbon-carbon triple bonds and having 2 to about 6 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic groups, aryl, alkoxy, aryloxy, alkyloxy, alkylcarbonyl, alkylcarboxy, amino, and arylthio which groups can be optionally substituted.

The term "acyl" as used herein refers to a carbonyl substituent, i.e., a C(O)(R) group where R is a straight- or branched-chain saturated aliphatic hydrocarbon group including, without limitation, alkyl, alkenyl, and alkynyl groups. Preferably, the R groups have 1 to about 8 carbon atoms, and more preferably 1 to about 6 carbon atoms. The term "substituted acyl" refers to an acyl group which is substituted with 1 or more groups including halogen, CN, OH, and $NO_2$.

The term "aryl" as used herein refers to an aromatic system which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted aryl group is substituted with 1 to about 4 substituents.

The term "heterocyclic" as used herein refers to a stable 4- to 7-membered monocyclic or multicyclic heterocyclic ring which is saturated, partially unsaturated, or wholly unsaturated. The heterocyclic ring has in its backbone carbon atoms and one or more heteroatoms including nitrogen, oxygen, and sulfur atoms. Preferably, the heterocyclic ring has about 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted heterocyclic group has 1 to 4 substituents.

The term "aroyl" as used herein refers to a carbonyl substituent bound to a phenyl or heterocyclic group. Preferably, the aroyl heterocyclic groups include 2-pyridinyl, 3-pyridinyl, 2-furanyl, 3-furanyl, 3-thiophenyl, 2-pyrimidinyl, and 4-pyrimidinyl groups. The term "substituted aroyl" refers to an aroyl group which is substituted with one or more groups including, without limitation, halogen, CN, OH, and $NO_2$.

The term "thioalkyl" as used herein is used interchangeably with the term "thioalkoxy", with both referring to an S(alkyl) group, where the point of attachment is through the sulfur-atom and the alkyl group can be optionally substituted.

The term "arylthio" as used herein refers to the S(aryl) group, where the point of attachment is through the sulfur-atom and the aryl group can be optionally substituted.

The term "alkoxy" as used herein refers to the O(alkyl) group, where the point of attachment is through the oxygen-atom and the alkyl group is optionally substituted. The term "aryloxy" as used herein refers to the O(aryl) group, where the point of attachment is through the oxygen-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The compounds of the present invention encompass tautomeric forms of the structures provided herein characterized by the bioactivity of the drawn structures. Further, the compounds of the present invention can be used in the form of salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates. Other conventional "pro-drug" forms can also be utilized which, when delivered in such form, convert to the active moiety in vivo.

These salts, as well as other compounds of the invention can be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233–241, ed., John Wiley & Sons (1996).

As described herein, the compounds of formula I and/or salts, prodrugs or tautomers thereof, are delivered in regimens which further involve delivery of SERMS.

The compounds discussed herein also encompass "metabolites" which are unique products formed by processing the compounds of the invention by the cell or patient. Preferably, metabolites are formed in vivo.

The SERMs used in the compositions and methods of the present invention can be chemically synthesized according to known methods, and include the salt forms of the compounds including tamoxifene (Nolvadex—AstraZeneca); 4-hydroxy-tamoxifene (AstraZeneca); raloxifene (Evista—Eli Lilly); droloxifene (Pfizer); toremifene (Fareston—Schering); iodotamoxifen (AstraZeneca); idoxifene (GSK); ICI182780 (Faslodex—AstraZeneca); EM-800 (Schering); EM-652 (Schering); arzoxifene (Eli Lilly); lasofoxifene (Pfizer); clomiphene (Clomid—Aventis); pipendoxifene (Wyeth); tibolone (Livial); levormeloxifene (Takeda and Novo Nordisk); centchroman (Saheli—Hindustan Latex and Centron—Torrent); bazedoxifene (Wyeth); and ZK186619 (Schering). Other SERMS include cycladiene (Dienestrol); nafoxidine; nitromifene citrate; 13-ethyl-17α-ethynyl-17β-hydroxygona-4-9-11-trien-3-one; diphenol hydrochryscne; erythro-MEA; allenolic acid; cyclofenyl; chlorotrianisene (TACE); ethamoxytriphetol (MER-25); triparanol; CI-626; CI-680; U-11,555A; U-11,100A; ICI-46,669; ICI-46,474; and CN-55,945 as described in U.S. Pat. No. 6,258,802. Preferably, the SERM is raloxifene hydrochloride, arzoxifene, lasofoxifene, droloxifene, tamoxifen citrate, 4-hydroxytamoxifen citrate, clomiphene citrate, toremifene citrate, pipendoxifene, or bazedoxifene.

The compounds of formula I and formula II useful in this invention can be prepared following the Schemes illustrated below.

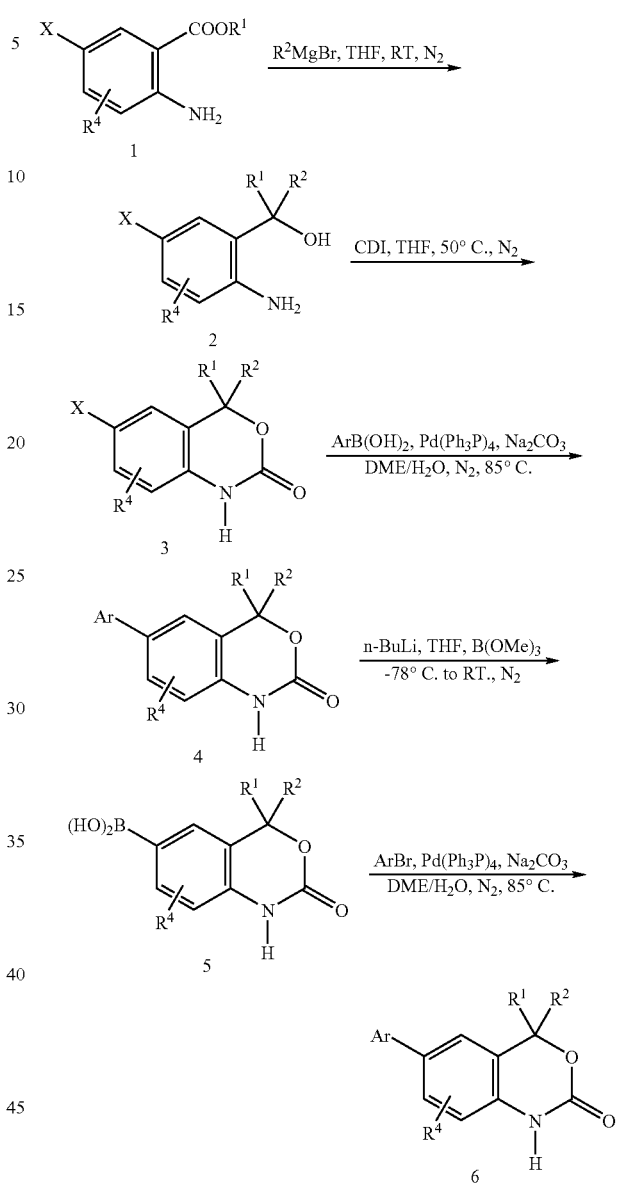

As demonstrated in Scheme I, the compounds useful in this invention are generally prepared by employing the suitable coupling reaction as a final step. An appropriately substituted ortho-amino benzoic acid or its derivatives such as ethyl ester (X=Br, I, Cl, or a latent coupling precursor such as alkoxy group which can be converted into a OTf group suitable in the coupling reaction) was treated with a suitable organometallic reagent, e.g., Grignard reagent, in appropriate nonprotic solvents which include, but are not limited to, THF or ether to give ortho-amino carbinol 2 under an inert atmosphere such as argon or nitrogen at −78° C. to room temperature. Ring closure of carbinol 2 to yield benzoxazin-2-one 3 is commonly effected by a condensing agent such as carbonyldiimidazole, phosgene, dimethylcarbonate, or diethylcarbonate in a suitable nonprotic solvent such as THF at temperatures ranging from room temperature to 65° C. The arylation of benzoxazin-2-one 3 to yield 4 can be effected by various coupling reactions including Suzuki, Stille reactions. These reactions are commonly performed in the presence of transition metallic catalyst, e.g., palladium or nickel complex often with phosphino ligands, e.g., Ph₃P, dppf, dppe or palladium acetate. Under this catalytic condition, an appropriately substituted nucleophilic reagent, e.g., aryl boronic acid, arylstannane, or aryl zinc compound, is coupled with benzoxazinone 3 to give 4. If a base is needed in the reaction, the commonly used bases include, but are not limited to, sodium bicarbonate, sodium carbonate, potassium phosphate, barium carbonate, or potassium acetate. The most commonly used solvents in these reactions include benzene, dimethylformamide (DMF), isopropanol, ethanol, dimethoxyethane (DME), ether, acetone, or a mixture of above solvents and water. The coupling reaction is generally executed under an inert atmosphere such as nitrogen or argon at temperatures ranging from room temperature to 95° C.

Benzoxazinone 3 can be converted into a nucleophile such as boronic acid which can be coupled with an appropriate electrophile, e.g., aryl bromide or aryl iodide, to yield 4 employing the coupling reaction condition as described above. The transformation of 3 into 5 can be effected by treating 3 with an organometallic reagent, e.g., n-BuLi, in a nonprotic solvent such as tetrahydrofuran (THF) or ether followed by quenching the reaction solution with a suitable electrophile, such as trimethyl borate, triisopropyl borate, or zinc chloride at temperatures ranging from −78° C. to room temperature under an inert atmosphere such as argon or nitrogen.

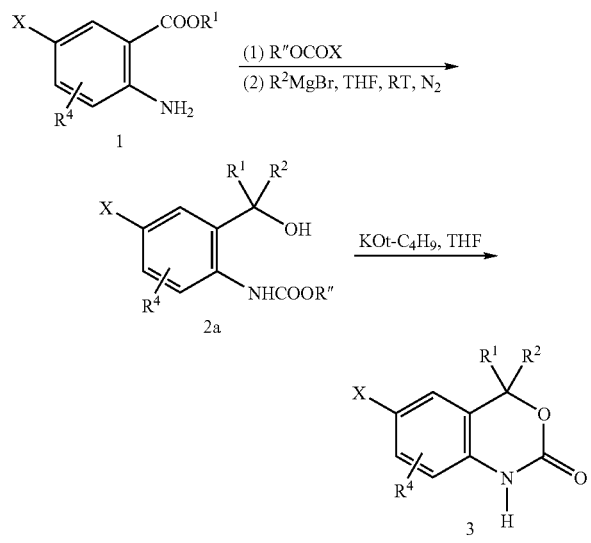

Scheme 1a illustrates an alternative approach leading to the benzoxazinone 3. Thus, an appropriate aniline 1 is protected with a suitable alkoxy carbonyl protective group including, but not limited to, allenoxy carbonyl, t-butoxy carbonyl, benzoxy carbonyl, ethoxy carbonyl, or methoxy carbonyl in a suitable solvent such as THF, acetonitrile, with or without presence of a base either as a catalyst or as an acid scavenger. The protected aniline is then treated with a suitable organometallic reagent such as an organolithium agent or Grignard reagent in the same fashion as to prepare compound 2 to give the carbinol 6. The treatment of 2a with a suitable base such as potassium t-butoxide, n-butyl lithium, potassium hydroxide in an appropriate solvent such as toluene, THF, alcohol under an inert atmosphere such as nitrogen or argon at temperatures ranging from room temperature to the boiling point of the relevant solvent to afford benzoxazinone 3.

Scheme II describes the procedures to prepare benzoxazinones bearing two different substituents at position-4. The Weinreb amide 8 can be prepared from an appropriately substituted isatoic anhydride 7 when treated with N-, O-dimethylhydroxyl-amine hydrochloride salt in a protic solvent such as ethanol, isopropanol at reflux under an inert atmosphere such as argon or nitrogen. Coupling of amide 8 with an aryl electrophile such as aryl boronic acid or arylstannane to give 9 can be effected by employing a typical coupling reaction such as Suzuki, Stille coupling procedure in a similar fashion as described for the preparation of benzoxazinones 4. Treatment of Weinreb amide 9 with organometallic compounds, e.g., alkyllithium, alkynyllithium, aryllithium, or their Grignard counterpart in a nonprotic solvent such as THF or ether under an inert atmosphere such as argon or nitrogen at −78° C. to room temperature affords amino ketone 10. Conversion of ketone 10 to carbinol 11 can be effected by treatment of 10 with an organometallic reagent such as alkyl, alkynyl, or aryl Grignard compound in a nonprotic solvent such as THF or ether under an inert atmosphere such as argon or nitrogen at −78° C. to room temperature. Conversion of ketone 10 to carbinol 11 can also be effected by reduction of ketone group of 10 to the carbinol moiety of 11 using an appropriate reducing reagent such as lithium aluminum hydride, sodium borohydride in a suitable solvent such as THF, ether, or anhydrous alcohol under an inert atmosphere in the temperature range from 0° C. to the boiling point of the solvent. Ring closure of carbinol 11 to produce the compounds of formulae I and II can be accomplished with condensing agents such as carbonyldiimidazole, phosgene, dimethylcarbonate, or diethylcarbonate in a suitable nonprotic solvent such as THF at temperatures ranging from room temperature to 65° C.

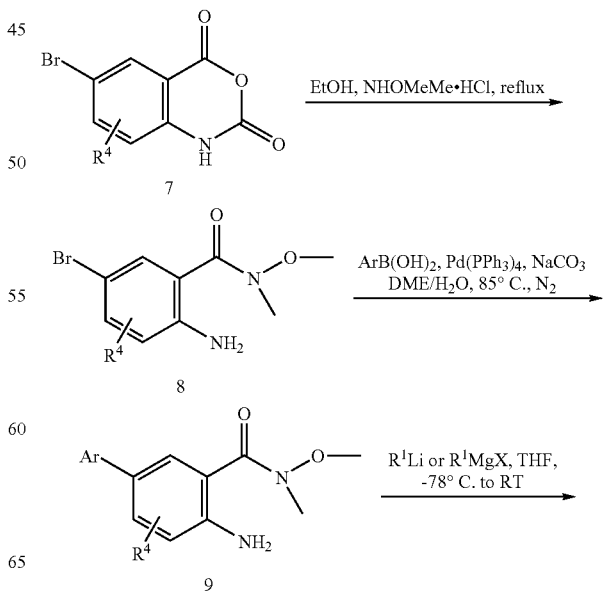

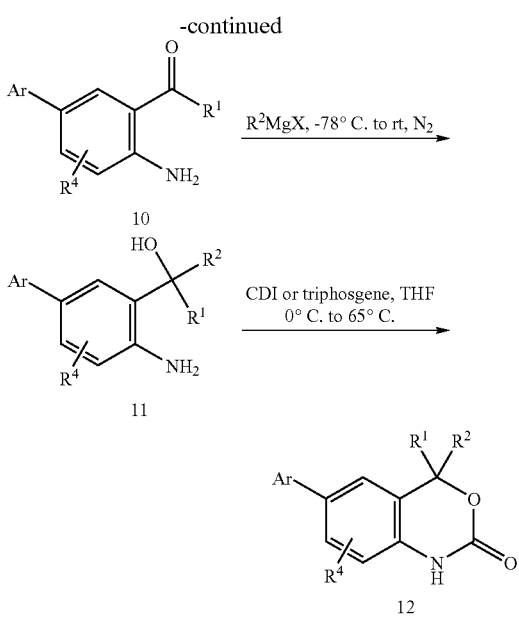

Alternatively, ortho-amino ketone 10 can be prepared by treatment of ortho-amino benzonitrile 14 with an organometallic compound such as organolithium reagent or Grignard reagent in a suitable solvent such as THF or ether under an inert atmosphere such as argon or nitrogen at temperatures ranging from −78° C. to room temperature as illustrated in Scheme III. Benzonitrile 14 can be readily prepared from an appropriately substituted benzonitrile such as bromobenzonitrile 13 using a suitable coupling reaction such as Stille or Suzuki protocol carried out in a similar fashion as described for the preparation of the Weinreb amide 9.

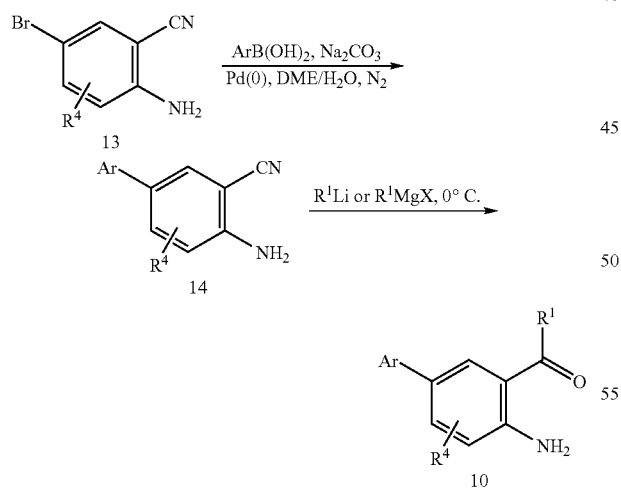

Scheme IV depicts an approach to prepare benzoxazinones with a low perfluoroalkyl substituent at position-4, e.g. $R^1$ is trifluoromethyl group. An appropriately substituted chloroaniline 15 was protected with a suitable protective group such as pivaloyl chloride or di-tert-butyl pyrocarbonate to give protected aniline 16 in a suitable solvent such as acetonitrile, acetone, THF, methylene chloride, or a mixture of solvent such as methylene chloride and water under an inert atmosphere such as argon or nitrogen at temperatures ranging from 0° C. to 70° C. A suitable base such as sodium carbonate, sodium bicarbonate, or potassium carbonate can be needed when the reaction produces an acid as a side-product such as hydrochloride. Treatment of 16 with an appropriate alkyllithium such as n-butyllithium or s-butyllithium followed by reaction with a low perfluorocarboxy derivatives, e.g., trifluoroacetyl chloride, 1-(trifluoroacetyl)-imidazole, or ethyl trifluoroacetate in a nonprotic solvent such as ether or THF under an inert atmosphere such as argon or nitrogen at −78° C. to ambient temperature gives the protective ortho-amino ketones. Subsequent removal of the protecting group can be effected by reaction of protected amino ketones with a suitable acid such as trifluoroacetate (TFA), 3N aqueous hydrochloride solution in a suitable solvent such as methylene chloride or water at 0° C. to boiling point of the solvent to afford ortho-amino ketone 17.

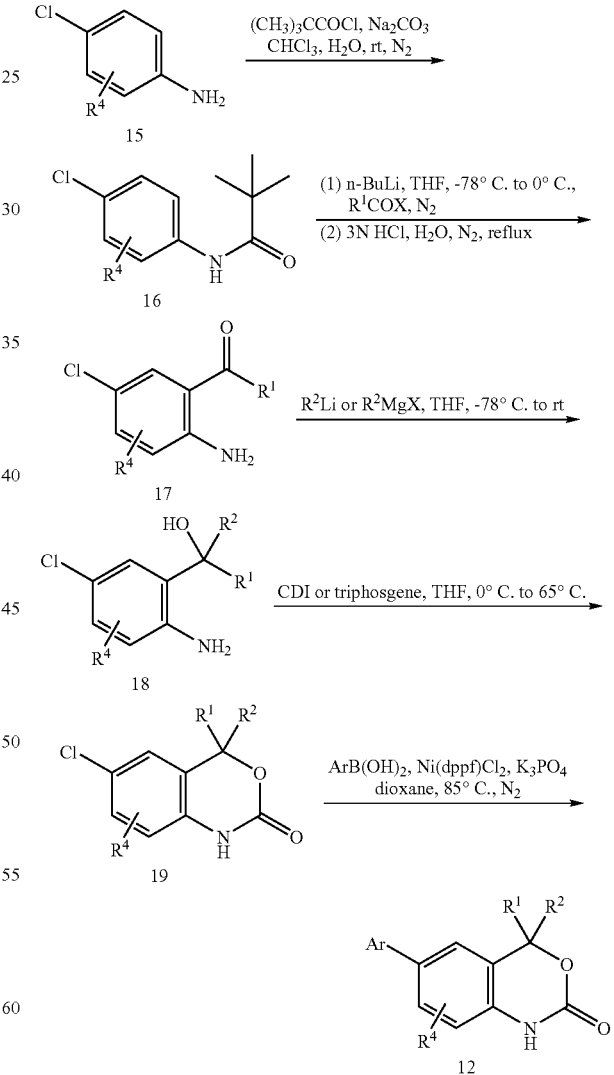

The preparation of 6-chlorobenzoxazinone 19 from 17 can be accomplished in the same fashion as described for the synthesis of benzoxazinone 12 from ketone 10. Coupling of 19 with an aryl group to yield 12 can be effected by a nickel complex catalyzed coupling reaction. The palladium catalysts proved not to be an efficient catalyst in this coupling process. The coupling reaction of 19 with an appropriate aryl boronic acid can be accomplished in the presence of a suitable base such as potassium phosphate and a catalyst of nickel (0 or II) complex, e.g. a nickel complex of 1,2-bis(diphenylphosphino)ethane, 1,1'-bis(diphenylphosphino)ferrocene, or triphenylphosphine. The most commonly used solvents in the reaction include dioxane or THF. The coupling reaction is generally executed under an inert atmosphere such as nitrogen or argon at temperatures ranging from ambient temperature to 95° C.

As described in Scheme V the conversion of benzoxazin-2-one 3 or 12 into benzoxazin-2-thione 20 or 21 can be accomplished by treatment of 3 or 12 with a suitable sulfur reagent such as Lawesson's reagent in a nonprotic solvent such as o-xylene, chlorobenzene, or toluene under an inert atmosphere such as argon or nitrogen at reflux.

at reflux. In a similar fashion, compound 23 can be formed by reaction of amino carbinol 11 with an appropriate imino-S, S-acetals or imino-acetals ($R^6$ is an electron withdrawing group) employing a procedure similar to that of Evers, et al. (I. Prakt. Chem. 333(5): 699–710 (1991)) or Haake et al. (Synthesis-Stuttgart 9: 753–758 (1991)) in a suitable solvent such as ethanol under an inert atmosphere such as argon or nitrogen at reflux. Other procedures (e.g. Wrobel et al. J. Med. Chem. 32: 2493(1989)) potentially leading to compounds 22 or 23 from 20 or 21 is illustrated in Scheme VIIa. Thus, compound 20 or 21 is alkylated with an appropriate alkylating agent such as the Meerwein reagent in a suitable solvent such as methylene chloride. This is then followed by a nucleophilic replacement of an appropriate nucleophile such as carbon anion or an amine base to give compounds 22 or 23, which can produce either tautomeric form of compounds 22 or 23.

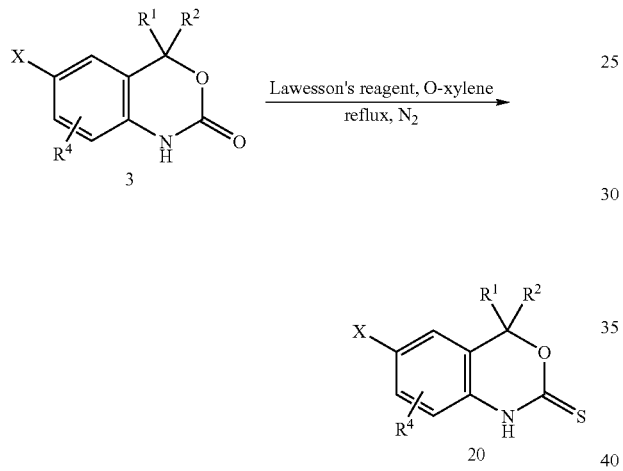

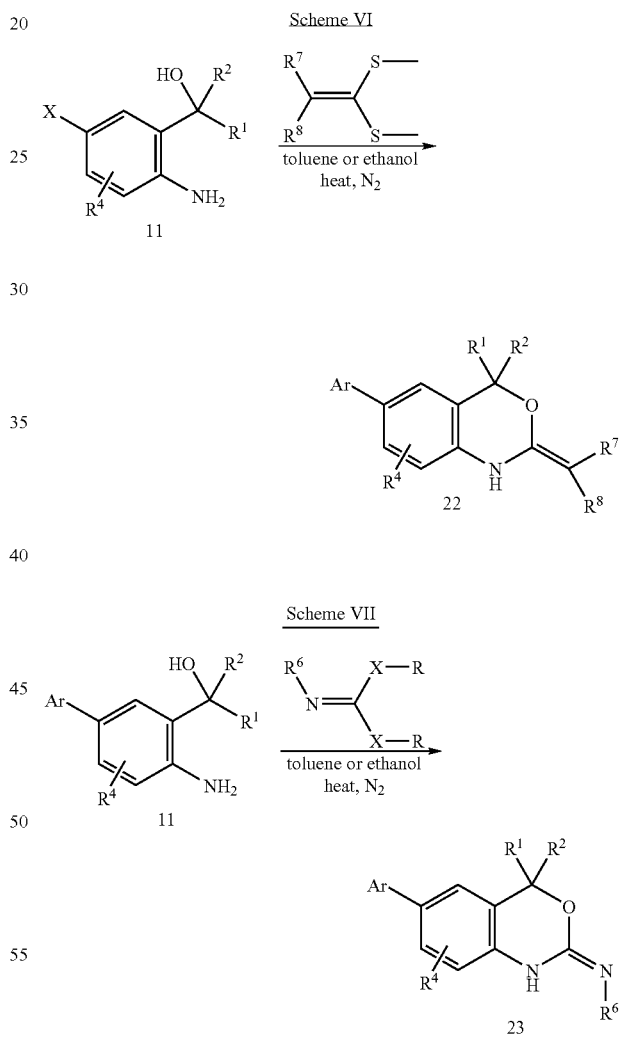

Schemes VI and VII describe the synthesis of other benzoxazinone bioisosteres. Using a similar procedure reported by Kondo et al. (Kondo, et al. J. Med. Chem. 33(7): 2012–2015 (1990)) compound 22 can be formed by treatment of amino carbinol 11 with an appropriate ketene-S, S-acetals (at least one of $R^7$ or $R^8$ is an electron withdrawing group) in a suitable solvent such as toluene or anhydrous ethanol under an inert atmosphere such as nitrogen or argon

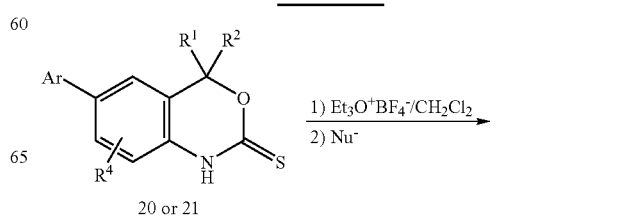

-continued

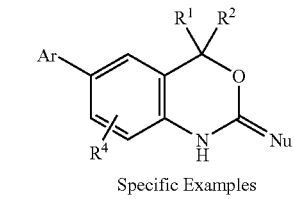

Specific Examples

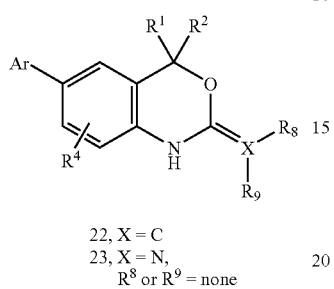

22, X = C
23, X = N,
R$^8$ or R$^9$ = none

As illustrated in Scheme VIII, the compound 21 can be further derivatized at position-1 via numerous approaches leading to a variety of the novel cyclothiocarbamate derivatives including 1-alkyl, substituted 1-alkyl, 1-carbonyl, substituted 1-carbonyl, 1-carboxy, substituted 1-carboxy derivatives. For example, alkyl or substituted alkyl derivatives 24 can be formed by treatment of thiocarbamate 12 or 6 with a suitable base such as sodium hydride in suitable solvent such as DMF under an inert atmosphere, such as argon or nitrogen, followed by addition of an appropriate electrophile such as alkyl or substituted alkyl bromide, iodide, or triflate. Such a transformation of 21 at position-1 can also be effected using a biphasic condition as indicated in Scheme VIII in which alkylation is executed using a biphasic catalyst such as tributylammonium bromide in a suitable solvent such as acetonitrile. A further example of such a modification includes, but is not limited to, heating 21 with triethyl orthoformate to afford 1-substituted derivatives 24. (Scheme VIII)

The acylation or carboxylation of the compound 21 at position-1 to give compound 25 can be readily effected by treatment of 12 or 6 with a suitable acylating or carboxylating reagent such as di-t-butyl dicarbonate in the presence of a suitable basic catalyst such as dimethylaminophenol (DMAP) in a suitable solvent such as acetonitrile under an inert atmosphere such as argon or nitrogen. The amination of position-1 of compound 21 to give compound 26 can be furnished using a suitable aminating reagent such as chloroamine in the presence of a suitable base such as sodium hydride in a suitable solvent such as THF or diethyl ether following the literature procedure (Metlesics et al. J. Org. Chem. 30: 1311(1965)).

Scheme VIII

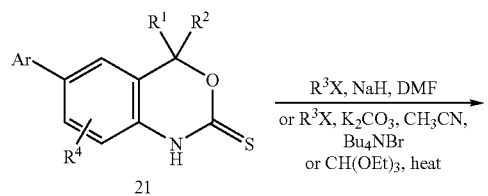

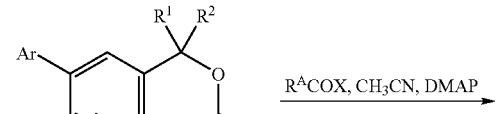

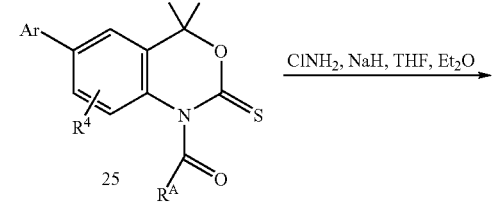

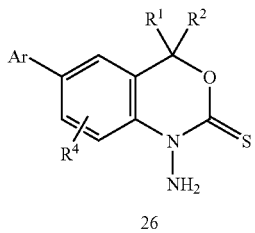

II. Formulations of the Invention

The compounds of formula I and formula II and the SERMS described herein can be formulated separately, or in a combined formulation, in any form suitable for the desired route of delivery using a pharmaceutically effective amount of one or more of the compounds of formula I, formula II, or combinations thereof. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral or transdermal. Optionally, the compounds of formula I and/or formula II are delivered in a regimen with one or more SERMS, but with each active component delivered by different routes.

A pharmaceutically effective amount of the compositions used according to the present invention can vary depending on the specific compositions, mode of delivery, severity of the hormone related condition being treated, and any other active ingredients used in the formulation or the selected regimen, among others. The dosing regimen can be adjusted to provide the optimal therapeutic response. Several divided doses can be delivered daily, e.g., in divided doses 2 to 4 times a day, or a single daily dose can be delivered. The dose can however be proportionally reduced or increased as indicated by the exigencies of the therapeutic situation. When the compound(s) of formula I or formula II and the SERM(s) are delivered separately, the dosing schedule for each can be the same, or can differ.

Preferably, the delivery can be on a daily, weekly, or monthly basis, and more preferably on a daily delivery. Daily dosages can be lowered or raised based on the periodic delivery.

Preferably, the compound(s) of formula I or formula II are delivered at a daily dosage of from about 0.1 to about 500 mg body weight, more preferably at a total daily dosage is from about 0.1 to about 100 mg, and most preferably from about 0.1 to about 50 mg. Preferably, the amount of SERM utilized according to the present invention is preferably at least 0.2 mg per day, more preferably from about 0.2 mg to about 200 mg per day, and most preferably from about 0.2 mg to about 100 mg per day, and most preferably from about 0.2 mg to about 100 mg, or about 5 mg to 50 mg, or 10 mg to 25 mg, per day. In some embodiments, particularly potent PR modulators (e.g., compounds of formula II) may be used at the lower end of these ranges. The compounds of formula I or formula II and/or the SERMs can be combined with one or more pharmaceutically acceptable carriers or excipients including, without limitation, solid and liquid carriers. Where formulated together, the components are selected to be compatible with the PR modulators used in the invention. Such carriers can include adjuvants, syrups, elixirs, diluents, binders, lubricants, surfactants, granulating agents, disintegrating agents, emollients, and combinations thereof.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Elixers and/syrups can be prepared from acceptable sweeteners such as sugar, saccharine or a biological sweetener, a flavoring agent, and/or solvent. In one embodiment, a syrup can contain about 10 to about 50% of a sugar carrier. In another embodiment, the elixir can contain about 20 to about 50% of an ethanol carrier.

Diluents can include materials in which the compositions can be dispersed, dissolved, or incorporated. Preferably, the diluents include water, lower monovalent alcohols, and low molecular weight glycols and polyols, including propylene glycol, diethylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers, oils such as corn, peanut and sesame oils, dimethylsulfoxide (DMSO), dimethylformamide (DMF), and combinations thereof. Preferably, the diluent is water.

Binders can include, without limitation, cellulose, methylcellulose, hydroxymethylcellulose, polypropylpyrrolidone, polyvinylpyrrolidone, gelatin, gum arabic, polyethylene glycol, starch, sugars such as sucrose, kaolin, and lactose, among others.

Lubricants can include magnesium stearate, light anhydrous silicic acid, talc and sodium lauryl sulfate, among others.

Granulating agents can include, without limitation, silicon dioxide, microcrystalline cellulose, starch, calcium carbonate, pectin, and crospovidone, polyplasdone, among others.

Disintegrating agents can include starch, carboxymethylcellulose, hydroxypropylstarch, substituted hydroxypropylcellulose, sodium bicarbonate, calcium phosphate, and calcium citrate, among others Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

III. Therapeutic Regimens

The present invention provides dosing regimens utilizing the compounds of formula I and/or formula II in combination with one or more selective estrogen receptor modulators. The compositions can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral or transdermal.

In one embodiment, the compositions are delivered orally by tablet, capsule, microcapsules, dispersible powder, granule, suspension, syrup, elixir, and aerosol. Desirably, when the compositions are delivered orally, delivery is by tablets and hard- or liquid-filled capsules.

In another embodiment, the compositions are delivered intravenously, intramuscularly, subcutaneously, parenterally and intraperitoneally in the form of sterile injectable solutions, suspensions, dispersions, and powders which are fluid to the extent that easy syringe ability exists. Such injectable compositions are sterile, stable under conditions of manufacture and storage, and free of the contaminating action of microorganisms such as bacteria and fungi.

Injectable formations can be prepared by combining the compositions with a liquid. The liquid can be selected from among water, glycerol, ethanol, propylene glycol and polyethylene glycol, oils, and mixtures thereof, and more preferably the liquid carrier is water. In one embodiment, the oil is vegetable oil. Optionally, the liquid carrier contains about a suspending agent. In another embodiment, the liquid carrier is an isotonic medium and contains about 0.05 to about 5% suspending agent.

In a further embodiment, the compositions are delivered rectally in the form of a conventional suppository.

In another embodiment, the compositions are delivered vaginally in the form of a conventional suppository, cream, gel, ring, or coated intrauterine device (IUD).

In yet another embodiment, the compositions are delivered intranasally or intrabronchially in the form of an aerosol.

In a further embodiment, the compositions are delivered transdermally or by sustained release through the use of a transdermal patch containing the composition and an optional carrier that is inert to the compound(s), is nontoxic to the skin, and allows for delivery of the compound(s) for systemic absorption into the blood stream. Such a carrier can be a cream, ointment, paste, gel, or occlusive device. The creams and ointments can be viscous liquid or semisolid emulsions. Pastes can include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., compositions of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compositions of the invention can be formulated as described herein. See, U.S. Pat. Nos. 3,845,770; 3,916,899; 3,536,809; 3,598,123; and 4,008,719.

The compositions of the invention, including compounds of formula I and/or formula II, and SERMS can be delivered (separately or together) using the same delivery route. Preferably, the compounds of formula I and/or formula II and SERMS are delivered orally or transdermally. Alternatively, the compounds of formula I and/or formula II and SERMS can be delivered using different delivery routes. In one embodiment, the SERM is delivered orally and the compound of formula I and/or formula II is delivery transdermally through the use of a patch.

The methods of the invention can include the continuous delivery of the compounds of formula I and/or formula II and/or SERMS. In another embodiment, the methods include the periodic discontinuation of the delivery of the compositions of the invention and/or SERMS. Such periodic discontinuation can include delivery of a placebo during the period of time where the compositions of the invention or SERMS are not delivered to the patient. Alternatively, no placebo or active agent is delivered to the patient when the compositions and SERMS are not being delivered to the patient.

By the term "placebo" or "inactive agent" is meant a reagent having pharmacological properties that are not relevant to the condition being treated, i.e., does not contain an active agent. Typical placebos include sugar as the primary constituent.

By the term "active agent" is meant any reagent which assists in treating a hormone-related condition.

The method of the present invention can be carried out over a cycle of 21 or more days, preferably 21 or more consecutive days, more preferably 21, 28, 30, or 31 days, and most preferably 21 or 28 days. One of skill in the art would readily be able to select and adjust the appropriate period of delivery.

The terminal portion of a cycle can be the last 1 to about 10 days of the cycle, and preferably the last 7 days of the cycle. In one embodiment, the terminal portion of the 28-day cycle can include the last 7 days of the cycle, i.e., days 22 to 28 of the 28-day cycle. The terminal portion of a cycle can include the delivery of an agent other than the compositions of the invention or SERMS and is preferably a placebo. Alternatively, no agent or placebo is delivered during the terminal portion of the cycle.

The regimen can include delivering a daily dosage of the compound of formula I and/or formula II and SERM, which are incorporated into a combined, single daily dosage unit. The regimen can also include delivering a single daily dosage unit of the compound of formula I and/or formula II and a single daily dosage unit of the SERM. Delivery of the compounds of formula I and/or formula II can be prior to, simultaneous with, or subsequent to the delivery of the SERM.

The regimen can further include alternating delivery of the compounds of formula I and/or formula II alone, the SERM alone, and a combination of the compound of formula I and/or formula II and the SERM. The regimen can also include the delivery of another reagent prior to, in conjunction with, or subsequent to the compound of formula I and/or formula II and the SERM.

The regimen can further include alternating delivery of the compounds of formula I and/or formula II alone, a SERM alone, and a combination of the compound of formula I and/or formula II and the SERM. The regimen can also include the delivery of another reagent prior to, in conjunction with, or subsequent to the compound of formula I and/or formula II and the SERM.

In one embodiment, a single combined daily dosage of the compound of formula I and/or formula II and a SERM can be delivered for the entire 21-day, 28-day, 30-day, or 31-day cycle. Alternatively, a single combined daily dosage of the compound of formula I and/or formula II and an SERM can be delivered for the first 21 days of a 28-day, 30-day, or 31-day cycle. A single combined daily dosage of the compound of formula I and/or formula II and an SERM can also be delivered for the first 24 days of a 28-day, 30-day, or 31-day cycle.

In a further embodiment, a daily dosage of the compound of formula I and/or formula II can be delivered by one route of delivery and a daily dosage of a SERM can be delivered by a second route of delivery for the entire 21-day, 28-day, 30-day, or 31-day cycle. Alternatively, a daily dosage of the compound of formula I and/or formula II can be delivered by one route of delivery and a daily dosage of a SERM can be delivered by a second route of delivery for the first 21 days of a 28-day, 30-day, or 31-day cycle. Further, a daily dosage of the compound of formula I and/or formula II can be delivered by one route of delivery and a daily dosage of a SERM can be delivered by a second route of delivery for the first 24 days of a 28-day, 30-day, or 31-day cycle.

In another embodiment, a daily dose of the compound of formula I and/or formula II can be delivered, followed by a daily dose of the SERM for the entire 21-day, 28-day, 30-day, or 31-day cycle. Alternatively, a daily dose of the compound of formula I and/or formula II can be delivered, followed by a daily dose of the SERM for the first 21 days of a 28-day, 30-day, or 31-day cycle. Alternatively, a daily dosage of the compound of formula I and/or formula II can be delivered, followed by a daily dosage of the SERM for the first 24 days of a 28-day, 30-day, or 31-day cycle.

In a further embodiment, the compounds of formula I and/or formula II are delivered with the SERM for the first 14 to 24 days of a 28-day cycle, followed by delivery of the SERM alone for a period of 1 to 11 days beginning on any cycle day between day 14 and 24.

In another embodiment, the compounds of formula I and/or formula II can be delivered for the initial 18 to 21 days of a 28-day cycle, followed by delivery of the SERM alone for from 1 to 7 days.

In yet a further embodiment, the compounds of formula I and/or formula II can be delivered alone over a 28 day cycle for the first 21 days, followed by delivery of a SERM alone from day 22 to day 24.

In another embodiment, the compounds of formula I and/or formula II and an estrogen can be delivered for the initial 21 days of a 28 day cycle, followed by a SERM alone from days 22 to 24.

The dosage regimens can be adjusted to provide the optimal therapeutic response. For example, several divided doses of each component can be delivered daily or the dose can be proportionally increased or reduced as indicated by the exigencies of the therapeutic situation. In the descriptions herein, reference to a daily dosage unit can also include divided units which are delivered over the course of each day of the cycle contemplated.

This invention further provides methods of treatment and dosing regimens further utilizing in combination with these progestins, estrogens such as ethinyl estradiol.

An isoflavone can alone be delivered or co-delivered with the compositions of the present invention in an amount sufficient to assist in the treatment of carcinomas. A number of isoflavones can be utilized and include, without limitation, genistein, daidzein, biochanin A, formononetin, and naturally occuring glucosides and glucoside conjugates. The amount of isoflavone sufficient to treat the carcinoma is dependent on the particular isoflavone utilized, the amount and activity of the co-delivered active agent, the size of the patient, the route of delivery, and the severity of the carcinoma. The amount of isoflavone sufficient to treat the hormone related condition is preferably at least 1 mg per day, more preferably from about 1 mg to about 1000 mg per day, and most preferably from about 50 mg to about 500 mg per day.

Estrogens can also be included in the compositions of the present invention. The estrogen can include natural estrogens, synthetic estrogens, catechol estrogens, conjugated estrogens, and non-steroidal estrogens, among others, or pharmaceutically acceptable salts or esters thereof. In one embodiment, the estrogen is a natural estrogen including estrone, including the acetate, propionate, sulfate, and sulfate piperazine ester salts; estradiol, including the 3-benzoate, 17b-cypionate, 17-proprionate, d-propionate, hemisuccinate, 17-heptanotate, 17-undecanoate, and 17-valerate ester salts; or estriol. In another embodiment, the estrogen is a synthetic estrogen including ethinyl estradiol. In a further embodiment, the estrogen is a conjugated estrogen including conjugated equine estrogens and sodium estrone sulfate and is available in formulations for intravenous, intramuscular, and topical administration (Wyeth). In a further embodiment, the estrogen is a catechol estrogen including 2- or 4-hydroxyestrogens. In yet another embodiment, the nonsteroidal estrogen is diethylstilbestrol. See, Chapter 50 entitled "Hormones" in Remington's Pharmaceutical Sciences, 18$^{th}$ Ed., Mack Publishing Company, Easton, Pa., 1990. The desired estrogen may however be selected from a variety of products commercially available. One of skill in the art would readily be able to select the estrogen, as well as dosage, that achieves the desired effect. Preferably, the estrogen is present in the formulation at about 0.01 mg to about 1.0 mg.

Other reagents can also be delivered in combination with the compositions of the present invention. Such reagents can include, chemotherapeutic agents, cytokines, androgens, and antiprogestins, among others. Preferably, the chemotherapeutic agents are taxol or cisplatin. Alternatively, such reagents can be alone administered prior or subsequent to the composition of the invention. In addition, the compositions of the invention can be delivered in conjunction with other cancer treatments, including radiation therapy and/or surgery.

As used herein, the terms "anti-progestational agents", "anti-progestins" and "progesterone receptor antagonists" are understood to be synonymous. Similarly, "progestins", "progestational agents" and "progesterone receptor agonists" are understood to refer to compounds of the same activity.

Optionally, progestins, other than those of formula I and/or formula II, can be delivered in combination with the compositions of the present invention. A number of progestins are known in the art and include, without limitation, progesterone, micronized progesterone, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl)norgestimate, among others. Preferably, the progestins are levonorgestrel, gestodene or trimegestone.

IV. Pharmaceutical Kits

The present invention provides kits or packages of pharmaceutical formulations designed for use in the regimens described herein. These kits are preferably designed for daily oral delivery over 21-day, 28-day, 30-day, or 31-day cycles, among others, and more preferably for one oral delivery per day. When the compositions and/or SERM are to be delivered continuously, a package or kit can include the composition and/or SERM in each tablet. When the compositions and/or SERM are to be delivered with periodic discontinuation, a package or kit can include placebos on those days when the composition and SERM are not delivered.

The kits are also preferably organized to indicate a single oral formulation or combination of oral formulations to be taken on each day of the cycle, preferably including oral tablets to be taken on each of the days specified, and more preferably one oral tablet will contain each of the combined daily dosages indicated.

In one embodiment, a kit can include a single phase of a daily dosage of the compound of formula I and/or formula II over a 21-day, 28-day, 30-day, or 31-day cycle. Alternatively, a kit can include a single phase of a daily dosage of the compound of formula I and/or formula II over the first 21 days of a 28-day, 30-day, or 31-day cycle. A kit can also include a single phase of a daily dosage of the compound of formula I and/or formula II over the first 28 days of a 30-day or 31-day cycle.

In a further embodiment, a kit can include a single combined phase of a daily dosage of the compound of formula I and/or formula II and a SERM over a 21-day, 28-day, 30-day, or 31-day cycle. Alternatively, a kit can include a single combined phase of a daily dosage of the compound of formula I and/or formula II and a SERM over the first 21 days of a 28-day, 30-day, or 31-day cycle. A kit can also include a single combined phase of a daily dosage of the compound of formula I and/or formula II and a SERM over the first 28 days of a 30-day or 31-day cycle.

In another embodiment, a 28-day kit can include a first phase of from 14 to 28 daily dosage units of the compound of formula I and/or formula II; a second phase of from 1 to 11 daily dosage units of a SERM; and, optionally, a third phase of an orally and pharmaceutically acceptable placebo for the remaining days of the cycle.

In yet a further embodiment, a 28-day kit can include a first phase of from 14 to 21 daily dosage units of the compound of formula I and/or formula II; a second phase of from 1 to 11 daily dosage units of a SERM; and, optionally, a third phase of an orally and pharmaceutically acceptable placebo for the remaining days of the cycle.

In another embodiment, a 28-day kit can include a first phase of from 18 to 21 daily dosage units of a compound of formula I and/or formula II; a second phase of from 1 to 7 daily dose units of a SERM; and, optionally, an orally and pharmaceutically acceptable placebo for each of the remaining 0 to 9 days in the 28-day cycle.

In a preferred embodiment, a 28-day kit can include a first phase of 21 daily dosage units of a compound of formula I and/or formula II; a second phase of 3 daily dosage units for days 22 to 24 of a SERM; and, optionally, a third phase of 4 daily units of an orally and pharmaceutically acceptable placebo for each of days 25 to 28.

Preferably, the daily dosage of each pharmaceutically active component of the regimen remain fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Preferably, the package has indicators for each day of the 28-day cycle, and more preferably is a labeled blister package, dial dispenser packages, or a bottle.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

1-Methyl-5-(2-thioxo-1,2-dihydrospiro[3,1-benzoxazine-4,1'-cyclobutan]-6-yl)-1H-pyrrole-2-carbonitrile A.
tert-Butyl[2-(1-hydroxycyclobutyl)phenyl]carbamate To phenyl-carbamic acid tert-butyl ester (2 g, 10.4 mmol) in ether (30 mL) at 0° C. was added t-BuLi (15 mL, 26 mmol, 1.7 M) and the reaction solution stirred for 3 hours prior to the addition of cyclobutanone (1.2 mL, 15.6 mmol). The reaction mixture was allowed to warm to room temperature. Upon completion by thin-layer chromatography (TLC), the reaction was poured into ice-cold saturated ammonium chloride (100 mL) and extracted with ethyl acetate (50 mL). The organics were dried over sodium sulfate, concentrated, and purified on a silica gel column (10% ethyl acetate/hexane) to give tert-butyl[2-(1-hydroxycyclobutyl)phenyl]carbamate (0.86 g, 32%) as a white solid. $^1$H NMR (DMSO-$d_6$): δ 8.48 (s, 1H), 7.8 (d, 1H, J=7.92 Hz), 7.35 (dd, 1H, J=7.7, 1.4 Hz), 7.25 (td, 1H, J=7.5, 1.6 Hz), 7.03 (td, 1H, J=7.5, 1.3 Hz), 2.51–2.49 (m, 2H), 2.43–2.39 (m, 2H), 2.28–2.25 (m, 2H), 1.45 (s, 9H). MS (ESI) m/z 190 ([M+H]$^+$); MS (ESI) m/z 188 ([M−H]$^−$);

B. Spiro[3,1-benzoxazine-4,1'-cyclobutan]-2(1H)-one

A solution of tert-butyl [2-(1-hydroxycyclobutyl)phenyl]carbamate (0.86 g, 3.3 mmol) in ethanol (30 mL) was stirred with potassium hydroxide (0.39 g, 6.9 mmol) at room temperature for 3 hours. The product was extracted with ethyl acetate (50 mL), dried with sodium sulfate, and concentrated to give spiro[3,1-benzoxazine-4,1'-cyclobutan]-2(1H)-one (0.36 g, 58%) as a white solid. $^1$H NMR (DMSO-$d_6$): δ 10.21 (s, 1H), 7.47 (dd, 1H, J=7.6, 1.2 Hz), 7.28 (td, 1H, J=7.6, 1.4 Hz), 7.08 (td, 1H, J=7.5, 1.2 Hz), 6.9 (dd, 1H, J=7.9, 0.9 Hz), 2.49–2.41 (m, 2H), 2.06–1.96 (m, 2H), 1.88–1.77 (m, 2H). MS (ESI) m/z 190 ([M+H]$^+$).

C. 6-Bromospiro[3,1-benzoxazine-4,1'-cyclobutan]-2(1H)-one

To a solution of spiro[3,1-benzoxazine-4,1'-cyclobutan]-2(1H)-one (0.36 g, 1.9 mmol) and potassium acetate (0.56 g, 5.7 mmol) in acetic acid was added a solution of bromine (0.09 mL, 1.95 mmol) in acetic acid (2 mL) at room temperature. Upon completion by TLC of the reaction, the acetic acid was removed. The residue was treated with saturated sodium bicarbonate (100 mL) and the product extracted with ethyl acetate (50 mL). The organics were dried over magnesium sulfate and concentrated. Trituration of residue with ether gave 6-bromospiro[3,1-benzoxazine-4,1'-cyclobutan]-2(1H)-one (0.27 g, 52%) as a white solid. $^1$H NMR (DMSO-$d_6$): δ 10.37 (s, 1H), 7.65 (d, 1H, J=2.1 Hz), 7.47 (dd, 1H, J=8.5, 2.2 Hz), 6.86 (d, 1H, J=8.5 Hz), 2.52–2.47 (m, 2H), 2.04–1.98 (m, 2H), 1.87–1.80 (m, 2H). MS (ESI) m/z 268/270 ([M+H]+); MS (ESI) m/z 266/268 ([M−H]−).

D. 1-Methyl-5-(2-oxo-1,2-dihydrospiro[3,1-benzoxazine-4,1'-cyclobutan]-6-yl)-1H-pyrrole-2-carbonitrile To a solution of 1-methyl-1H-pyrrole-2-carbonitrile (0.84 g, 7.1 mmol) and triisopropylborate (1.8 mL, 7.8 mmol) in THF (15 mL) at 0° C. was added lithium diisopropylamide (4.6 mL, 9.2 mmol). The reaction was allowed to warm to room temperature. Upon completion by TLC, the reaction was added dropwise to a 65° C. solution of 6-bromospiro[3,1-benzoxazine-4,1'-cyclobutan]-2(1H)-one (0.38 g, 1.4 mmol), potassium carbonate (0.58 g, 4.2 mmol) dissolved in (5 mL water), and tetrakistriphenylphosphine palladium (0) (0.081 g, 0.07 mmol) in tetrahydrofuran (10 mL). Upon completion by TLC of the reaction the reaction mixture was poured into a saturated solution of ammonium chloride (100 mL), extracted with ethyl acetate (50 mL), dried with magnesium sulfate, and purified on a silica gel column (40% ethyl acetate/hexane) to give 1-methyl-5-(2-oxo-1,2-dihydrospiro[3,1-benzoxazine-4,1'-cyclobutan]-6-yl)-1H-pyrrole-2-carbonitrile (0.33 g, 79%) as a light red solid. $^1$H NMR (DMSO-$d_6$): δ 10.41 (s, 1H), 7.58 (d, 1H, J=2 Hz), 7.43 (dd, 1H, J=8.2, 1.8 Hz), 7.04 (d, 1H, J=4.0 Hz), 6.39 (d, 1H, J=8.2 Hz), 6.39 (d, 1H, J=4.0 Hz), 3.73 (s, 3H), 2.55–2.49 (m, 2H), 2.05–1.90 (m, 2H), 1.88–1.83 (m, 2H). MS (ESI) m/z 294 ([M+H]+); MS (ESI) m/z 292 ([M−H]−). High resolution mass spectrometry (HRMS): calcd for $C_{17}H_{15}N_3O_2$, 293.1164; found (ESI_FT), 294.12311.

A solution of 1-methyl-5-(2-oxo-1,2-dihydrospiro[3,1-benzoxazine-4,1'-cyclobutan]-6-yl)-1H-pyrrole-2-carbonitrile (0.33 g, 1.1 mmol) and Lawesson's Reagent (0.23 g, 0.55 mmol) in toluene (10 mL) was heated at 100° C. Upon completion by TLC, the reaction mixture was poured into saturated sodium carbonate (100 mL) and extracted with ethyl acetate (50 mL), dried over magnesium sulfate, and concentrated. Trituration of the residue with ether (20 mL) gave 1-methyl-5-(2-thioxo-1,2-dihydrospiro[3,1-benzoxazine-4,1'-cyclobutan]-6-yl)-1H-pyrrole-2-carbonitrile (0.17 g, 49%) as a tan solid. $^1$H NMR (DMSO-$d_6$): δ 12.35 (s, 1H), 7.64 (d, 1H, J=2.0 Hz), 7.51 (dd, 1H, J=8.2, 2.0 Hz), 7.15 (d, 1H, J=8.3 Hz), 7.05 (d, 1H, J=4.03 Hz), 6.43 (d, 1H, J=4.03 Hz), 3.73 (s, 3H), 2.59–2.53 (m, 2H), 2.09–2.02 (m, 2H), 1.93–1.85 (m, 2H). MS (ESI) m/z 310 ([M+H]+); MS (ESI) m/z 308 ([M−H]−); HRMS: calcd for $C_{17}H_{15}N_3OS$, 309.0936; found (ESI_FT), 310.10057.

EXAMPLE 2

5-(4,4-Diethyl-2-thioxo-1,4-dihydro-2H-3,1-benzoxazin-6-yl)-1-methyl-1H-pyrrole-2-carbonitrile A. 5-(4,4-Diethyl-2-oxo-1,4-dihydro-2H-3,1-benzoxazin-6-yl)-1-methyl-1H-pyrrole-2-carbonitrile To a solution of 1-methyl-1H-pyrrole-2-carbonitrile (4.1 g, 35 mmol) and triisopropylborate (8.9 mL, 38.5 mmol) in THF (80 mL) at 0° C. was added lithium diisopropylamide (22.8 mL, 45.5 mmol). The reaction mixture was allowed to warm to room temperature. Upon completion by TLC, the reaction was added dropwise to a 65° C. solution of 6-bromo-4,4-diethyl-1,4-dihydro-benzo[d][1,3]oxazin-2-one (2.0 g, 7.0 mmol), potassium carbonate (2.9 g, 21 mmol) dissolved in (25 mL water), and tetrakistriphenylphosphine palladium (0) (0.4 g, 0.35 mmol) in tetrahydrofuran (20 mL). Upon completion by TLC of the reaction, it was poured into a saturated solution of ammonium chloride (200 mL), extracted with ethyl acetate (100 mL), dried with magnesium sulfate, and concentrated. Trituration of the residue with ethyl acetate/dichloromethane gave 5-(4,4-diethyl-2-oxo-1,4-dihydro-2H-3,1-benzoxazin-6-yl)-1-methyl-1H-pyrrole-2-carbonitrile (1.2 g, 55%) as an off-white solid. $^1$H NMR (DMSO-$d_6$): δ10.26 (s, 1H), 7.37 (d, 1H, J=8.2, 1.6 Hz), 7.31 (d, 1H, J=1.8 Hz), 7.03 (d, 1H, J=4.0 Hz), 6.96 (d, 1H, J=8.2 Hz), 6.32 (d, 1H, J=4.0 Hz), 3.69 (s, 3H), 2.02 (m, 2H, J=7.3 Hz), 1.88 (m, 2H, J=7.3 Hz), 0.78 (t, 6H, J=7.3 Hz). MS (ESI) m/z 310 ([M+H]$^+$); MS (ESI) m/z 308 ([M−H]$^−$). HRMS: calcd for $C_{18}H_{19}N_3O_2$, 309.1477; found (ESI_FT), 310.15488;

5-(4,4-diethyl-2-oxo-1,4-dihydro-2H-3,1-benzoxazin-6-yl)-1-methyl-1H-pyrrole-2-carbonitrile (0.5 g, 1.6 mmol) and Lawesson's Reagent (0.33 g, 0.81 mmol) were heated to 100° C. in toluene (20 mL). Upon completion by TLC, the reaction was poured into saturated sodium carbonate (100 mL) and extracted with ethyl acetate (50 mL), dried over magnesium sulfate, and concentrated. The purification with column gave 5-(4,4-diethyl-2-thioxo-1,4-dihydro-2H-3,1-benzoxazin-6-yl)-1-methyl-1H-pyrrole-2-carbonitrile (0.040 g, 8%) as a tan solid. $^1$H NMR (DMSO-$d_6$): δ 12.15 (s, 1H), 7.44 (d, 1H, J=8.3, 1.8 Hz), 7.37 (d, 1H, J=1.8 Hz), 7.12 (d, 1H, J=8.3 Hz), 7.04 (d, 1H, J=4.03 Hz), 6.35 (d, 1H, J=4.2 Hz), 3.7 (s, 3H), 2.07 (m, 2H, J=7.4 Hz), 1.95 (m, 2H, J=7.4 Hz), 0.79 (t, 6H, J=7.4 Hz). MS (ESI) m/z 326 ([M+H]+); MS (ESI) m/z 324 ([M−H]−). HRMS: calcd for $C_{18}H_{19}N_3OS$, 325.1249; found (ESI_FT), 326.13187.

EXAMPLE 3

5-(4-ethyl-4-methyl-2-thioxo-1,4-dihydro-2H-3,1-benzoxazin-6-yl)-1-methyl-1H -pyrrole-2-carbonitrile A. 6-Bromo-4-ethyl-4-methyl-1,4-dihydro-2H-3,1-benzoxazin-2-one To a stirred solution of 1-(2-amino-5-bromophenyl)-ethanone (10.00 g, 46.70 mmol) in THF (150 mL) was added 3.0M ethyl magnesium bromide (50 mL, 150 mmol) slowly at 0° C. over 20 minutes. The reaction was stirred 1 hr at 0° C., quenched with ammonium chloride solution (sat.) and extracted with ethyl acetate several times. The organic layer was washed with brine and dried over magnesium sulfate. The concentrated crude material was dissolved in THF (150 mL). 1,1'-Carbonyldiimidazole (9.00 g, 56.04 mmol) was added and the reaction was stirred overnight at room temperature. The reaction was partitioned between ammonium chloride solution (sat.) and ethyl acetate. The organic layer was dried over magnesium sulfate and concentrated. Flash silica gel column separation with 30% ethyl acetate/hexane followed by trituration with ether gave 6-bromo-4-ethyl-4-methyl-1,4-dihydro-2H-3,1-benzoxazin-2-one as a white solid (5.84 g, 46%). $^1$H NMR (DMSO-$d_6$): δ 10.28 (s, 1H), 7.43 (m, 2H), 6.783 (d, J=8.3 Hz, 1H), 2.02 (m, 1H), 1.87 (m, 1H), 1.57 (s, 3H), 0.82 (t, J=7.3 Hz, 3H). MS (ESI) m/z 270/272 ([M+H]$^+$); MS (ESI) m/z 268/270 ([M−H]$^−$); HRMS: calcd for $C_{11}H_{12}BrNO_2$, 269.0051; found (ESI_FT), 270.01259. Anal. Calcd for $C_{11}H_{12}BrNO_2$: C, 48.91; H, 4.48; N, 5.19. Found: C, 48.94; H, 4.38; N, 5.00.

B. 5-(4-Ethyl-4-methyl-2-oxo-1,4-dihydro-2H-3,1-benzoxazin-6-yl)-1-methyl-1H-pyrrole-2-carbonitrile Prepared from 6-bromo-4-ethyl-4-methyl-1,4-dihydro-2H-3,1-benzoxazin-2-one and 1-methyl-1H-pyrrole-2-carbonitrile according to procedure of example 1. $^1$H NMR (DMSO-$d_6$): δ 10.32 (s, 1H), 7.39 (dd, J=8.2, 2.0 Hz, 1H), 7.36 (d, J=2.0 Hz, 1H), 7.03 (d, J=4.2 Hz, 1H), 6.98 (d, J=8.1 Hz, 1H), 6.33 (d, J=4.0 Hz, 1H), 3.70 (s, 3H), 2.06 (m, 1H), 1.90 (m, 1H), 1.61 (s, 3H), 0.85 (t, J=7.3 Hz, 3H). MS (ESI) m/z 296 ([M+H]$^+$); MS (ESI) m/z 294 ([M−H]$^−$). HRMS: calcd for $C_{17}H_{17}N_3O_2$, 295.1321; found (ESI_FT), 296.13872. Anal. Calcd for $C_{17}H_{17}N_3O_2$: C, 69.14; H, 5.80; N, 14.23. Found: C, 68.89; H, 5.60; N, 13.98.

The title compound was prepared from 5-(4-ethyl-4-methyl-2-oxo-1,4-dihydro-2H-3,1-benzoxazin-6-yl)-1-methyl-1H-pyrrole-2-carbonitrile. $^1$H NMR (DMSO-$d_6$): δ 12.23 (s, 1H), 7.47 (dd, J=8.2, 1.2 Hz, 1H), 7.42 (d, J=1.3 Hz, 1H), 7.14 (d, J=8.3 Hz, 1H), 7.04 (dd, J=4.2, 0.7 Hz, 1H), 6.37 (dd, J=4.2, 0.7 Hz, 1H), 3.71 (s, 3H), 2.08 (m, 1H), 1.95 (m, 1H), 1.67 (s, 3H), 0.87 (t, J=7.3 Hz, 3H). MS (ESI) m/z 312 ([M+H]$^+$); MS (ESI) m/z 310 ([M−H]$^−$); HRMS: calcd for $C_{17}H_{17}N_3OS$, 311.1092; found (ESI_FT), 312.11619. Anal. Calcd for $C_{17}H_{17}N_3OS$: C, 65.57; H, 5.50; N, 13.49. Found: C, 65.29; H, 5.51; N, 13.24.

EXAMPLE 4

1-Methyl-5-(2-thioxo-1,2-dihydrospiro[3,1-benzoxazine-4,1'-cyclohexan]-6-yl)-1H-pyrrole-2-carbonitrile A. 1-Methyl-5-(2-oxo-1,2-dihydrospiro[3,1-benzoxazine-4,1'-cyclohexan]-6-yl)-1H-pyrrole-2-carbonitrile Prepared from 6-bromospiro[4H-3,1-benzoxazine-4,1'-cyclohexan]-2(1H)-one and 1-methyl-1H-pyrrole-2-carbonitrile according to the procedure of example 1. $^1$H NMR (DMSO-$d_6$): δ 10.33 (s, 1H), 7.40 (m, 2H), 7.03 (d, J=4.0 Hz, 1H), 6.98 (d, J=8.2 Hz, 1H), 6.33 (d, J=4.0 Hz, 1H), 3.70 (s, 3H), 2.0 (d, J=5.2 Hz, 2H), 1.97 (td, J=13.5, 4.0 Hz, 2H), 1.76 (m, 4H), 1.67 (m, 2H). MS (ESI) m/z 322 ([M+H]$^+$); MS (ESI) m/z 320 ([M−H]$^−$). HRMS: calcd for $C_{19}H_{19}N_3O_2$, 321.1477; found (ESI_FT), 322.15457; Anal. Calcd for $C_{19}H_{19}N_3O_2$: C, 71.01; H, 5.96; N, 13.07. Found: C, 70.59; H, 5.53; N, 12.38.

The title compound was prepared from 1-methyl-5-(2-oxo-1,2-dihydrospiro[3,1-benzoxazine-4,1'-cyclohexan]-6-yl)-1H-pyrrole-2-carbonitrile according to the procedure of example 1. $^1$H NMR (DMSO-$d_6$): δ12.29 (s, 1H), 7.47 (m, 2H), 7.14 (d, J=7.3 Hz, 1H), 7.04 (d, J=4.2 Hz, 1H), 6.37 (d, J=4.0 Hz, 1H), 3.71 (s, 3H), 2.03 (d, J=13.2 Hz, 2H), 1.95 (td, J=12.7, 3.9 Hz, 2H), 1.82 (m, 4H), 1.63 (d, J=12.5 Hz, 2H). MS (ESI) m/z 338 ([M+H]$^+$); MS (ESI) m/z 336 ([M−H]$^−$); HRMS: calcd for $C_{19}H_{19}N_3OS$, 337.1249; found (ESI_FT), 338.13141.

EXAMPLE 5

1-Methyl-5-(2-thioxo-1,2-dihydrospiro[3,1-benzoxazine-4,1'-cyclopentan]-6-yl)-1H-pyrrole-2-carbonitrile

A. 1-Methyl-5-(2-oxo-1,2-dihydrospiro[3,1-benzoxazine-4,1'-cyclopentan]-6-yl)-1H-pyrrole-2-carbonitrile Prepared from 6-bromospiro[4H-3,1-benzoxazine-4,1'-cyclopentan]-2(1H)-one and 1-methyl-1H-pyrrole-2-carbonitrile according to the procedure of example 1. $^1$H NMR (DMSO-d$_6$): δ 10.35 (s, 1H), 7.40 (m, 2H), 7.02 (d, J=4.2 Hz, 1H), 6.99 (d, J=8.4 Hz, 1H), 6.34 (d, J=4.0 Hz, 1H), 3.70 (s, 3H), 2.15 (m, 4H), 1.89 (m, 4H). MS (ESI) m/z 308 ([M+H]$^+$); MS (ESI) m/z 306 ([M−H]$^−$); HRMS: calcd for C$_{18}$H$_{17}$N$_3$O$_2$, 307.1321; found (ESI_FT), 308.13868; Anal. Calcd for C$_{18}$H$_{17}$N$_3$O$_2$: C, 70.34; H, 5.58; N, 13.67. Found: C, 70.27; H, 5.57; N, 13.74.

The title compound was prepared from 1-methyl-5-(2-oxo-1,2-dihydrospiro[3,1-benzoxazine-4,1'-cyclopentan]-6-yl)-1H-pyrrole-2-carbonitrile according to the procedure of example 1. $^1$H NMR (DMSO-d$_6$): δ 12.29 (s, 1H), 7.48 (m, 2H), 7.14 (d, J=8.7 Hz, 1H), 7.04 (d, J=4.0 Hz, 1H), 6.38 (d, J=4.2 Hz, 1H), 3.71 (s, 3H), 2.19 (m, 4H), 1.93 (m, 4H). MS (ESI) m/z 324 ([M+H]$^+$); MS (ESI m/z 322 ([M−H]$^−$); HRMS: calcd for C$_{18}$H$_{17}$N$_3$OS, 323.1092; found (ESI_FT), 324.11637; Anal. Calcd for C$_{18}$H$_{17}$N$_3$OS: C, 66.85; H, 5.30; N, 12.99. Found: C, 65.84; H, 5.22; N, 12.30.

EXAMPLE 6

1-Methyl-5-[2-thioxo-4,4-bis(trifluoromethyl)-1,4-dihydro-2H-3,1-benzoxazin-6-yl]-1H-pyrrole-2-carbonitrile

A. 2-(2-Aminophenyl)-1,1,1,3,3,3-hexafluoropropan-2-ol

To a stirred solution of phenylcarbamic acid tert-butyl ester (2.00 g, 10.35 mmol) in ether (20 mL) was added 1.7M tert-butyl lithium (14 mL, 22.80 mmol) at −10° C. The reaction was stirred for 3 hrs at −10° C., cooled to −78° C. and gaseous hexafluoroacetone was bubbled into the solution for 5 minutes. The reaction was allowed to warm to room temperature, quenched with ammonium chloride solution (sat.) and extracted with ethyl acetate. The organic layer was dried over magnesium sulfate and concentrated. The crude concentrate was stirred in excess trifluoroacetic acid for 20 minutes. The solution was concentrated, neutralized with sodium bicarbonate solution (sat.) and extracted several times with ethyl acetate. The organic layer was dried over magnesium sulfate and concentrated to give 4.20 g of 2-(2-aminophenyl)-1,1,1,3,3,3-hexafluoropropan-2-ol as white solid (52%). $^1$H NMR (DMSO-d$_6$): δ 9.29 (s, 1H), 7.16 (m, 2H), 6.77 (dd, J=8.2, 1.2 Hz, 1H), 6.62 (m, 1H), 5.63 (br s, 2H). MS (ESI) m/z 260 ([M+H]$^+$); MS (ESI) m/z 258 ([M−H]$^−$); HRMS: calcd for C$_9$H$_7$F$_6$NO, 259.0432; found (ESI_FT), 260.04993.

B. 4,4-Bis(trifluoromethyl)-1,4-dihydro-2H-3,1-benzoxazin-2-one

To a stirred solution of 2-(2-aminophenyl)-1,1,1,3,3,3-hexafluoropropan-2-ol (4.20 g, 16.20 mmol) in THF (160 mL) was added triphosgene (4.80 g, 16.20 mmol). The reaction was stirred overnight, quenched with ammonium chloride solution (sat.) and extracted several times with ethyl acetate. The organic layer was dried over magnesium sulfate and triturated with ether/hexane to give 2.78 g of 4,4-bis(trifluoromethyl)-1,4-dihydro-2H-3,1-benzoxazin-2-one as a tan solid (60%). $^1$H NMR (DMSO-d$_6$): δ 11.37 (s, 1H), 7.62 (m, 2H), 7.29 (t, J=7.5 Hz, 1H), 7.11 (dd, J=8.0, 0.8 Hz, 1H). MS (ESI) m/z 284 ([M−H]$^−$); HRMS: calcd for C$_{10}$H$_5$F$_6$NO$_2$, 285.0224; found (ESI_FT), 286.0299; Anal. Calcd for C$_{10}$H$_5$F$_6$NO$_2$: C, 42.12; H, 1.77; N, 4.91. Found: C, 42.63; H, 1.79; N, 4.72.

C. 6-Bromo-4,4-bis(trifluoromethyl)-1,4-dihydro-2H-3,1-benzoxazin-2-one

To a stirred solution of 4,4-bis(trifluoromethyl)-1,4-dihydro-2H-3,1-benzoxazin-2-one (0.50 g, 1.75 mmol) in glacial acetic acid (6 mL) buffered with potassium acetate (0.52 g, 5.25 mmol) was added bromine (0.28 g, 1.75 mmol). The reaction was stirred 30 minutes and poured into brine (30 mL), and extracted with ethyl acetate several times. The organic layer was dried over magnesium sulfate and concentrated. Flash column separation using 10% ethyl acetate/hexane gave 0.36 g of 6-bromo-4,4-bis(trifluoromethyl)-1,4-dihydro-2H-3,1-benzoxazin-2-one as a white solid(57%). $^1$H NMR (DMSO-d$_6$): δ 11.57 (s, 1H), 7.85 (dd, J=8.7, 2.2 Hz, 1H), 7.60 (s, 1H), 7.08 (d, J=8.7 Hz, 1H). MS (ESI) m/z 362/364 ([M+H]$^+$); HRMS: calcd for C$_{10}$H$_4$BrF$_6$NO$_2$, 362.9330; found (ESI_FT), 363.93994.

D. 1-Methyl-5-[2-oxo-4,4-bis(trifluoromethyl)-1,4-dihydro-2H-3,1-benzoxazin-6-yl]-1H-pyrrole-2-carbonitrile Prepared from 6-bromo-4,4-bis(trifluoromethyl)-1,4-dihydro-2H-3,1-benzoxazin-2-one and 1-methyl-1H-pyrrole-2-carbonitrile according to the procedure of example 1. $^1$H NMR (DMSO-d$_6$): δ 11.59 (s, 1H), 7.78 (dd, J=8.5, 2.0 Hz, 1H), 7.57 (s, 1H), 7.22 (d, J=8.4 Hz, 1H), 7.06 (d, J=4.0 Hz, 1H), 6.39 (d, J=4.2 Hz, 1H), 3.69 (s, 3H). MS (ESI) m/z 388 ([M−H]$^−$); HRMS: calcd for C$_{16}$H$_9$F$_6$N$_3$O$_2$, 389.0599; found (ESI_FT), 390.0659.

The title compound was prepared from 1-methyl-5-[2-oxo-4,4-bis(trifluoromethyl)-1,4-dihydro-2H-3,1-benzoxazin-6-yl]-1H-pyrrole-2-carbonitrile according to the procedure of example 1. $^1$H NMR (DMSO-d$_6$): δ 13.43 (s, 1H), 7.85 (dd, J=8.5, 1.8 Hz, 1H), 7.62 (s, 1H), 7.37 (d, J=8.6 Hz, 1H), 7.07 (d, J=4.0 Hz, 1H), 6.44 (d, J=4.2 Hz, 1H), 3.70 (s, 3H). MS (ESI) m/z 406 ([M+H]$^+$); MS (ESI m/z 404 ([M−H]$^−$); HRMS: calcd for C$_{16}$H$_9$F$_6$N$_3$OS, 405.0370; found (ESI_FT), 406.04395.

EXAMPLE 7

Breast Carcinoma Study

MCF-7 breast carcinoma cells are plated in 24-well dishes in phenol-red free DMEM:F-12 (1:1) medium containing antibiotics, β-mercaptoethanol, ethanolamine, sodium selenite and 5% charcoal-stripped FCS. The compositions of the invention and vehicle are added the following day and refreshed with media change every 48 hours. Cultures are stopped 9 days later and proliferation assayed using the Cyquant kit (Molecular Probes, Eugene, Oreg.).

The results of this experiment illustrate the therapeutic effect the compositions of the invention have on the treatment of breast carcinoma.

EXAMPLE 8

Dysfunctional Uterine Bleeding Study

Thirty women are selected for the study. The women are randomly divided into two groups, one of which receives a regimen of the invention, and the other of which receives a placebo. The patients are evaluated as to the character of their dysfunctional uterine bleeding (blood loss, timing, etc.) prior to the study's initiation.

Women in the test group receive between 50–200 mg of the drug per day by the oral route. This therapy continues for 6 months. Utility of the compositions of the invention is illustrated by the therapeutic effect they have on the patients' dysfunctional uterine bleeding.

EXAMPLE 9

Anti-androgenic Effect

The androgen receptor (AR) agonistic and antagonistic activity of the compositions of the invention in the L929 cells which express the AR but not the PR was evaluated as described in Zhang et al., Steroids, 65(10–11): 637–643 (October–November 2000).

Cells were plated in 96-well plates at 25,000 cells/well in DMEM (Bio Whittaker) with 10% (v/v) fetal bovine serum (FBS). The next day, cells were infected with the adenovirus PRE-tk-luciferase reporter construct ($2 \times 10^9$ pfu/ml particles) and kept in DMEM containing 10% charcoal stripped FBS for an additional 24 hours. Cells were then separately treated with a range of concentrations of the dihydrotestosterone (DHT) reference, the 2-hydroxyflutamide (2-OH-fluta) reference, or 5-(4,4-dimethyl-2-thioxo-1,4-dihydro-2H-3,1-benzoxazin-6-yl)-1-methyl-1H-pyrrole-2-carbonitrile diluted in the same medium. To test the anti-androgenic activity, cells were co-treated with 3 nM DHT. Luciferase activity was measured 24 hours following the treatment. The following data were obtained:

TABLE 1

| Compound | IC50 (nM) |
| --- | --- |
| 5-(4,4-dimethyl-2-thioxo-1,4-dihydro-2H-3,1-benzoxazin-6-yl)-1-methyl-1H-pyrrole-2-carbonitrile | 109 |
| 2-OH-fluta | 49.9 |

From these data, it was noted that 5-(4,4-dimethyl-2-thioxo-1,4-dihydro-2H-3,1-benzoxazin-6-yl)-1-methyl-1H-pyrrole-2-carbonitrile showed significant antagonistic activity over a nine point dose response and only marginal agonistic activity at the maximum concentration tested (i.e., 10 nM).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of inducing contraception comprising the step of delivering to a female of child-bearing age a composition comprising a compound of formula II in a regimen which involves delivering a pharmaceutically effective amount of one or more of a selective estrogen receptor modulator to said female, wherein formula II is:

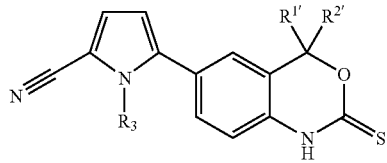

wherein:
  $R^{1'}$ is selected from the group consisting of methyl, ethyl, and trifluoromethyl;
  $R^{2'}$ is selected from the group consisting of methyl, ethyl, and trifluoromethyl; or
  $R^{1'}$ and $R^{2'}$ are joined to form a spirocyclic ring containing 3 to 7 carbon atoms; and
  $R^{3'}$ is $C_1$ to $C_4$alkyl;
or a pharmaceutically acceptable salt, tautomer, metabolite, or prodrug of formula II.

2. The method according to claim 1, wherein said compound of formula II and said selective estrogen receptor modulator are delivered in a single composition.

3. The method according to claim 1, wherein said compound of formula II and said selective estrogen receptor modulator are delivered separately.

4. The method according to claim 1, wherein said selective estrogen receptor modulator is selected from the group consisting of EM-800, EM-652, raloxifene hydrochloride, arzoxifene, lasofoxifene, droloxifene, idoxifene, levormeloxifene, centchroman, nafoxidene, tamoxifen citrate, 4-hydroxytamoxifen citrate, clomiphene citrate, toremifene citrate, pipendoxifene, and bazedoxifene.

5. The method according to claim 1, wherein said compound is delivered at a daily dosage of about 0.1 to about 50 mg.

6. The method according to claim 1, wherein said regimen comprises delivering said composition daily for 1 to about 21 days, wherein said regimen is a cycle which is repeated monthly.

7. The method according to claim 1, wherein said selective estrogen receptor modulator is delivered at a daily dosage of about 0.2 to about 100 mg.

8. The method according to claim 1 wherein said compound is selected from the group consisting of 5-(4,4-Dimethyl-2-thioxo-1,4-dihydro-2H-3,1-benzoxazin-6-yl)-1-methyl-1H-pyrrole-2-carbonitrile, and 5-(4,4-dimethyl-2-thioxo-1,4-dihydro-2H-3,1-benzoxazin-6-yl)-1-ethyl-1H-pyrrole-2-carbonitrile, or a pharmaceutically acceptable salt, tautomer, metabolite, or prodrug thereof.

9. The method according to claim 1, wherein said compound of formula II is selected from the group consisting of: 5-(4-ethyl-4-methyl-2-thioxo-1,4-dihydro-2H-3,1-benzoxazin-6-yl)-1-methyl-1H-pyrrole-2-carbonitrile, 5-(4,4-diethyl-2-thioxo-1,4-dihydro-2H-3,1-benzoxazin-6-yl)-1-methyl-1H-pyrrole-2-carbonitrile, 1-methyl-5-(2-thioxo-1,2-dihydrospiro[3,1-benzoxazine-4,1'-cyclobutan]-6-yl)-1H-pyrrole-2-carbonitrile, 1-methyl-5-(2-thioxo-1,2-dihydrospiro[3,1-benzoxazine-4,1'-cyclohexan]-6-yl)-1H-pyrrole-2-carbonitrile, 1-methyl-5-(2-thioxo-1,2-dihydrospiro[3,1-benzoxazine-4,1'-cyclopentan]-6-yl)-1H-pyrrole-2-carbonitrile, 1-methyl-5-[2-thioxo-4,4-bis(trifluoromethyl)-1,4-dihydro-2H-3,1-benzoxazine-6-yl]-1H-pyrrole-2-carbonitrile, and prodrugs, metabolites, and pharmaceutically acceptable salts thereof.

10. A pharmaceutical kit useful for inducing contraception, said kit comprising a compound of formula II and at least one selective estrogen receptor modulator, wherein formula II is:

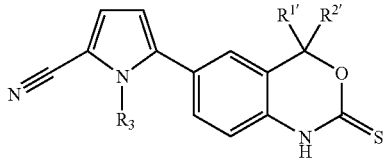

wherein:
  $R^{1'}$ is selected from the group consisting of methyl, ethyl, and trifluoromethyl;
  $R^{2'}$ is selected from the group consisting of methyl, ethyl, and trifluoromethyl; or
  $R^{1'}$ and $R^{2'}$ are joined to form a spirocyclic ring containing 3 to 7 carbon atoms; and
  $R^{3'}$ is $C_1$ to $C_4$alkyl;
or a pharmaceutically acceptable salt, tautomer, metabolite, or prodrug thereof.

11. A contraceptive regimen comprising the periodic and discontinuous delivery of a compound of formula II and a pharmaceutically effective amount of one or more of a selective estrogen receptor modulator to a female of child-bearing age, wherein formula II is:

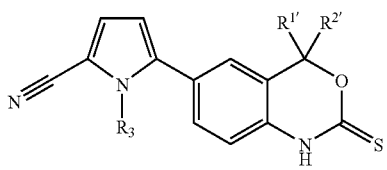

wherein:
  $R^{1'}$ is selected from the group consisting of methyl, ethyl, and trifluoromethyl;
  $R^{2'}$ is selected from the group consisting of methyl, ethyl, and trifluoromethyl; or
  $R^{1'}$ and $R^{2'}$ are joined to form a spirocyclic ring containing 3 to 7 carbon atoms; and
  $R^{3'}$ is $C_1$ to $C_4$ alkyl;
or a pharmaceutically acceptable salt, tautomer, metabolite, or prodrug of formula II.

12. The regimen according to claim 11, comprising delivering said compound of formula II and said selective estrogen receptor modulator separately.

13. The regimen according to claim 11, comprising delivering said compound of formula II and said selective estrogen receptor modulator in a single composition.

14. The regimen according to claim 11, further comprising delivering a placebo.

15. The regimen according to claim 11 which comprises 28 days.

16. The regimen according to claim 15, wherein said regimen comprises delivering said compound of formula II and said selective estrogen receptor modulator for 14 to 24 days.

17. A contraceptive regimen comprising the periodic and discontinuous delivery of a compound of formula II and a pharmaceutically effective amount of one or more of a selective estrogen receptor modulator to a female of child-bearing age, wherein formula II is:

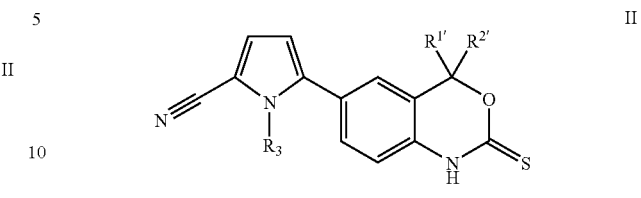

wherein:
  $R^{1'}$ is selected from the group consisting of methyl, ethyl, and trifluoromethyl;
  $R^{2'}$ is selected from the group consisting of methyl, ethyl, and trifluoromethyl; or
  $R^{1'}$ and $R^{2'}$ are joined to form a spirocyclic ring containing 3 to 7 carbon atoms; and
  $R^{3'}$ is $C_1$ to $C_4$ alkyl;
or a pharmaceutically acceptable salt, tautomer, metabolite, or prodrug of formula II, and wherein said regimen comprises:
  (a) delivering said compound of formula II and said selective estrogen receptor modulator for the first 14 to 24 days of a 28 day regimen; and
  (b) delivering said selective estrogen receptor modulator alone for 1 to 11 days beginning on any day between days 14 and 24.

18. The regimen according to claim 17, wherein said regimen further comprises:
  (c) delivering a placebo for 1 to 10 days during the period of time where said compound of formula II and said selective estrogen receptor modulator are not delivered.

19. A contraceptive regimen comprising the periodic and discontinuous delivery of a compound of formula I or II and a pharmaceutically effective amount of one or more of a selective estrogen receptor modulator to a female of child-bearing age, wherein formula I is:

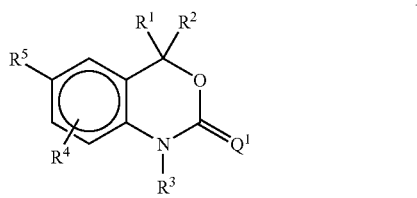

wherein:
  $R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, carbon-based heterocyclic ring having in its backbone 1 to 3 heteroatoms, substituted carbon-based heterocyclic ring having in its backbone 1 to 3 heteroatoms, $COR^4$, and $NR^BCOR^4$;
  or $R^1$ and $R^2$ are fused to form a ring selected from the group consisting of a), b) and c), wherein said ring is optionally substituted by from 1 to 3 substituents selected from the group consisting of H and $C_1$ to $C_3$ alkyl;

a) a carbon-based 3 to 8 membered saturated spirocyclic ring;

b) a carbon-based 3 to 8 membered spirocyclic ring having one or more carbon-carbon double bonds; and c) a 3 to 8 membered spirocyclic ring having in its backbone one to three heteroatoms selected from the group consisting of O, S and N;

$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl;

$R^B$ is selected from the group consisting of H, $C_1$ to $C_3$ alkyl, and substituted $C_1$ to $C_3$ alkyl;

$R^3$ is selected from the group consisting of H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, and $COR^C$;

$R^C$ is selected from the group consisting of H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, and substituted $C_1$ to $C_4$ aminoalkyl;

$R^4$ is selected from the group consisting of H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ selected from the group consisting of (i) and (ii):

(i) a substituted benzene ring having the structure:

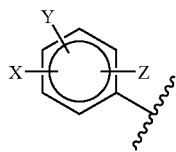

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $COR^D$, $OCOR^D$, and $NR^ECOR^D$;

$R^D$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^E$ is selected from the group consisting of H, $C_1$ to $C_3$ alkyl, and substituted $C_1$ to $C_3$ alkyl;

Y and Z are independent substituents selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl; and (ii) a five or six membered carbon-based heterocyclic ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $C_1$ to $C_3$ thioalkyl, substituted $C_1$ to $C_3$ thioalkyl, $COR^F$, and $NR^GCOR^F$;

$R^F$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, $C_1$ to $C_3$ alkyl, and $C_1$ to $C_4$ $CO_2$alkyl;

$Q^1$ is selected from the group consisting of S, $NR^7$, and $CR^8R^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $SO_2CF_3$, $OR^{11}$, and $NR^{11}R^{12}$;

$R^8$ and $R^9$ are independent substituents selected from the group consisting of H, $C^1$ to $C^6$ alkyl, substituted $C^1$ to $C^6$ alkyl, $C^3$ to $C^8$ cycloalkyl, substituted $C^3$ to $C^8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $NO_2$, CN, and $CO_2R^{10}$;

$R^{10}$ is selected from the group consisting of $C_1$ to $C_3$ alkyl and substituted $C_1$ to $C_3$ alkyl;

or $CR^8R^9$ comprise a six membered ring having the structure:

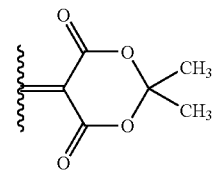

$R^{11}$ and $R^{12}$ are independently selected from the group consisting of H, $C_1$ to $C_6$ alkyl, substituted $C_1$ to $C_6$ alkyl, aryl, substituted aryl, carbon-based heterocyclic ring having in its backbone 1 to 3 heteroatoms, substituted carbon-based heterocyclic ring having in its backbone 1 to 3 heteroatoms, acyl, substituted acyl, sulfonyl, and substituted sulfonyl;

and formula II is:

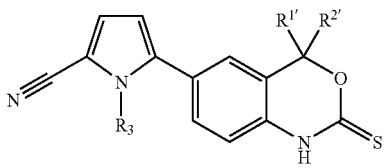

wherein:
R$^{1'}$ is selected from the group consisting of methyl, ethyl, and trifluoromethyl;
R$^{2'}$ is selected from the group consisting of methyl, ethyl, and trifluoromethyl; or
R$^{1'}$ and R$^{2'}$ are joined to form a spirocyclic ring containing 3 to 7 carbon atoms;
and
R$^{3'}$ is C$_1$ to C$_4$ alkyl;
or a pharmaceutically acceptable salt, tautomer, metabolite, or prodrug of formula I or formula II, wherein said regimen comprises:
(a) delivering said compound of formula I or formula II for the first 18 to 21 days of a 28 day regimen; and
(b) delivering said selective estrogen receptor modulator alone for 1 to 7 days following delivery of (a).

20. A contraceptive regimen comprising the periodic and discontinuous delivery of a compound of formula I or II and a pharmaceutically effective amount of one or more of a selective estrogen receptor modulator to a female of child-bearing age, wherein formula I is:

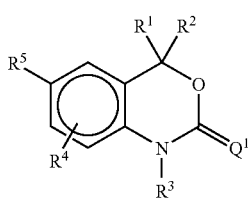

wherein:
R$^1$ and R$^2$ are independent substituents selected from the group consisting of H, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, carbon-based heterocyclic ring having in its backbone 1 to 3 heteroatoms, substituted carbon-based heterocyclic ring having in its backbone 1 to 3 heteroatoms, COR$^A$, and NR$^B$COR$^A$;
or R$^1$ and R$^2$ are fused to form a ring selected from the group consisting of a), b) and c), wherein said ring is optionally substituted by from 1 to 3 substituents selected from the group consisting of H and C$_1$ to C$_3$ alkyl;
a) a carbon-based 3 to 8 membered saturated spirocyclic ring;
b) a carbon-based 3 to 8 membered spirocyclic ring having one or more carbon-carbon double bonds; and
c) a 3 to 8 membered spirocyclic ring having in its backbone one to three heteroatoms selected from the group consisting of O, S and N;
R$^A$ is selected from the group consisting of H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, amino, C$_1$ to C$_3$ aminoalkyl, and substituted C$_1$ to C$_3$ aminoalkyl;
R$^B$ is selected from the group consisting of H, C$_1$ to C$_3$ alkyl, and substituted C$_1$ to C$_3$ alkyl;
R$^3$ is selected from the group consisting of H, OH, NH$_2$, C$_1$ to C$_6$ alkyl, substituted C$_1$ to C$_6$ alkyl, C$_3$ to C$_6$ alkenyl, substituted C3 to C6 alkenyl, alkynyl, substituted alkynyl, and COR$^C$;
R$^C$ is selected from the group consisting of H, C$_1$ to C$_4$ alkyl, substituted C$_1$ to C$_4$ alkyl, aryl, substituted aryl, C$_1$ to C$_4$ alkoxy, substituted C$_1$ to C$_4$ alkoxy, C$_1$ to C$_4$ aminoalkyl, and substituted C$_1$ to C$_4$ aminoalkyl;
R$^4$ is selected from the group consisting of H, halogen, CN, NO$_2$, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, and substituted C$_1$ to C$_6$ aminoalkyl;
R$^5$ is selected from the group consisting of (i) and (ii):
(i) a substituted benzene ring having the structure:

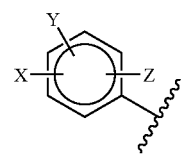

X is selected from the group consisting of halogen, CN, C$_1$ to C$_3$ alkyl, substituted C$_1$ to C$_3$ alkyl, C$_1$ to C$_3$ alkoxy, substituted C$_1$ to C$_3$ alkoxy, C$_1$ to C$_3$ thioalkyl, substituted C$_1$ to C$_3$ thioalkyl, C$_1$ to C$_3$ aminoalkyl, substituted C$_1$ to C$_3$ aminoalkyl, NO$_2$, C$_1$ to C$_3$ perfluoroalkyl, substituted C$_1$ to C$_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, COR$^D$, OCOR$^D$, and NR$^E$COR$^D$;
R$^D$ is selected from the group consisting of H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, and substituted C$_1$ to C$_3$ aminoalkyl;
R$^E$ is selected from the group consisting of H, C$_1$ to C$_3$ alkyl, and substituted C$_1$ to C$_3$ alkyl;
Y and Z are independent substituents selected from the group consisting of H, halogen, CN, NO$_2$, C$_1$ to C$_3$ alkoxy, substituted C$_1$ to C$_3$ alkoxy, C$_1$ to C$_4$ alkyl, substituted C$_1$ to C$_4$ alkyl, C$_1$ to C$_3$ thioalkyl, and substituted C$_1$ to C$_3$ thioalkyl; and
(ii) a five or six membered carbon-based heterocyclic ring having in its backbone 1, 2, or 3 heteroatoms selected from the group consisting of O, S, SO, SO$_2$, and NR$^6$ and having one or two independent substituents selected from the group consisting of H, halogen, CN, NO$_2$, C$_1$ to C$_4$ alkyl, substituted C$_1$ to C$_4$ alkyl, C$_1$ to C$_3$ alkoxy, substituted C$_1$ to C$_3$ alkoxy, C$_1$ to C$_3$ aminoalkyl, substituted C$_1$ to C$_3$ aminoalkyl, C$_1$ to C$_3$ perfluoroalkyl, substituted C$_1$ to C$_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, C$_1$ to C$_3$ thioalkyl, substituted C$_1$ to C$_3$ thioalkyl, COR$^F$, and NR$^G$COR$^F$;
R$^F$ is selected from the group consisting of H, C$_1$ to C$_3$ alkyl, substituted C$_1$ to C$_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, $C_1$ to $C_3$ alkyl, and $C_1$ to $C_4$ $CO_2$alkyl;

$Q^1$ is selected from the group consisting of S, $NR^7$, and $CR^8R^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $SO_2CF_3$, $OR^{11}$, and $NR^{11}R^{12}$;

$R^8$ and $R^9$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $NO_2$, CN, and $CO_2R^{10}$;

$R^{10}$ is selected from the group consisting of $C_1$ to $C_3$ alkyl and substituted $C_1$ to $C_3$ alkyl;

or $CR^8R^9$ comprise a six membered ring having the structure:

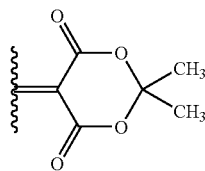

$R^{11}$ and $R^{12}$ are independently selected from the group consisting of H, $C_1$ to $C_6$ alkyl, substituted $C_1$ to $C_6$ alkyl, aryl, substituted aryl, carbon-based heterocyclic ring having in its backbone 1 to 3 heteroatoms, substituted carbon-based heterocyclic ring having in its backbone 1 to 3 heteroatoms, acyl, substituted acyl, sulfonyl, and substituted sulfonyl;

and formula II is:

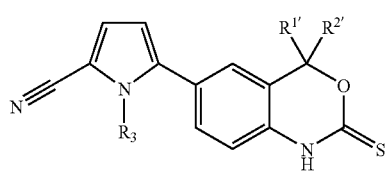

wherein:

$R^{1'}$ is selected from the group consisting of methyl, ethyl, and trifluoromethyl;

$R^{2'}$ is selected from the group consisting of methyl, ethyl, and trifluoromethyl; or $R^{1'}$ and $R^{2'}$ are joined to form a spirocyclic ring containing 3 to 7 carbon atoms;

and $R^{3'}$ is $C_1$ to $C_4$ alkyl;

or a pharmaceutically acceptable salt, tautomer, metabolite, or prodrug of formula I or formula II, wherein said regimen comprises:

(a) delivering said compound of formula I or formula II and a selective estrogen receptor modulator for the first 21 days of a 28 day regimen; and (b) delivering said selective estrogen receptor modulator alone from days 22 to 24 of said 28 day regimen.

21. A contraceptive regimen comprising the periodic and discontinuous delivery of a compound of formula I or II and a pharmaceutically effective amount of one or more of a selective estrogen receptor modulator to a female of childbearing age, wherein formula I is:

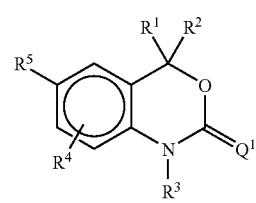

wherein:

$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, carbon-based heterocyclic ring having in its backbone 1 to 3 heteroatoms, substituted carbon-based heterocyclic ring having in its backbone 1 to 3 heteroatoms, $COR^A$, and $NR^BCOR^A$;

or $R^1$ and $R^2$ are fused to form a ring selected from the group consisting of a), b) and c), wherein said ring is optionally substituted by from 1 to 3 substituents selected from the group consisting of H and $C_1$ to $C_3$ alkyl;

a) a carbon-based 3 to 8 membered saturated spirocyclic ring;

b) a carbon-based 3 to 8 membered spirocyclic ring having one or more carbon-carbon double bonds; and c) a 3 to 8 membered spirocyclic ring having in its backbone one to three heteroatoms selected from the group consisting of O, S and N;

$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl;

$R^B$ is selected from the group consisting of H, $C_1$ to $C_3$ alkyl, and substituted $C_1$ to $C_3$ alkyl;

$R^3$ is selected from the group consisting of H, OH, $NH_2$, $C_1$ to C6 alkyl, substituted $C_1$ to $C_6$ alkyl, $C_3$ to $C_6$ alkenyl, substituted $C_3$ to $C_6$ alkenyl, alkynyl, substituted alkynyl, and $COR^C$;

$R^C$ is selected from the group consisting of H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, and substituted $C_1$ to $C_4$ aminoalkyl;

$R^4$ is selected from the group consisting of H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is selected from the group consisting of (i) and (ii):

(i) a substituted benzene ring having the structure:

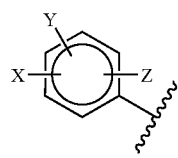

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $COR^D$, $OCOR^D$, and $NR^ECOR^D$;

$R^D$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^E$ is selected from the group consisting of H, $C_1$ to $C_3$ alkyl, and substituted $C_1$ to $C_3$ alkyl;

Y and Z are independent substituents selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl; and (ii) a five or six membered carbon-based heterocyclic ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $C_1$ to $C_3$ thioalkyl, substituted $C_1$ to $C_3$ thioalkyl, $COR^F$, and $NR^GCOR^F$;

$R^F$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, $C_1$ to $C_3$ alkyl, and $C_1$ to $C_4$ $CO_2$alkyl;

$Q^1$ is selected from the group consisting of S, $NR^{7'}$ and $CR^8R^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $SO_2CF_3$, $OR^{11}$, and $NR^{11}R^{12}$;

$R^8$ and $R^9$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $NO_2$, CN, and $CO_2R10$;

$R^{10}$ is selected from the group consisting of $C_1$ to $C_3$ alkyl and substituted $C_1$ to $C_3$ alkyl;

or $CR^8R^9$ comprise a six membered ring having the structure:

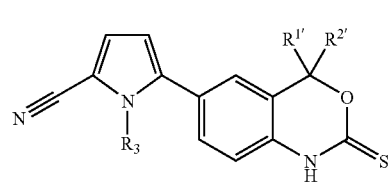

II $R^{11}$ and $R^{12}$ are independently selected from the group consisting of H, $C_1$ to $C_6$ alkyl, substituted $C_1$ to $C_6$ alkyl, aryl, substituted aryl, carbon-based heterocyclic ring having in its backbone 1 to 3 heteroatoms, substituted carbon-based heterocyclic ring having in its backbone 1 to 3 heteroatoms, acyl, substituted acyl, sulfonyl, and substituted sulfonyl;

and formula II is:

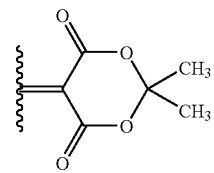

wherein:

$R^{1'}$ is selected from the group consisting of methyl, ethyl, and trifluoromethyl;

$R^{2'}$ is selected from the group consisting of methyl, ethyl, and trifluoromethyl; or $R^{1'}$ and $R^{2'}$ are joined to form a spirocyclic ring containing 3 to 7 carbon atoms; and $R^{3'}$ is $C_1$ to $C_4$ alkyl;

or a pharmaceutically acceptable salt, tautomer, metabolite, or prodrug of formula I or formula II, wherein said regimen comprises 28 days and the steps of:

(a) a first phase of the compound of formula I or formula II and said selective estrogen receptor modulator to be administered for the first 14 to 24 days of said regimen;

(b) a second phase of said selective estrogen receptor modulator to be administered for 1 to 11 days of said regimen beginning on any day between days 14 and 24; and (c) a third phase of an orally and pharmaceutically acceptable placebo being administered for 1 to 10 days excluding the days on which phase (a) or (b) occurs.

22. The regimen according to claim 21, wherein:

(a) said first phase comprises 14 days;

(b) said second phase comprises 7 days; and (c) said third phase comprises 7 days.

* * * * *

UNITED STATES PATENT AND TRADEMARK OFFICE
CERTIFICATE OF CORRECTION

PATENT NO. : 7,192,956 B2  Page 1 of 4
APPLICATION NO. : 10/601481
DATED : March 20, 2007
INVENTOR(S) : Fensome et al.

It is certified that error appears in the above-identified patent and that said Letters Patent is hereby corrected as shown below:

(1)  Col. 2, line 7, replace "mean" with -- meant --.
(2)  Col. 8, lines 20-30, replace the following structure:

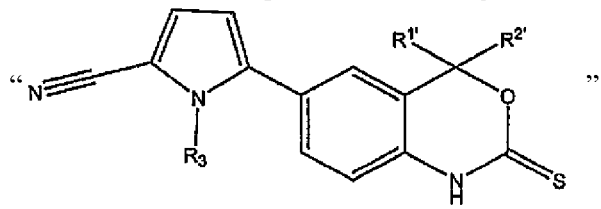

with the following structure:

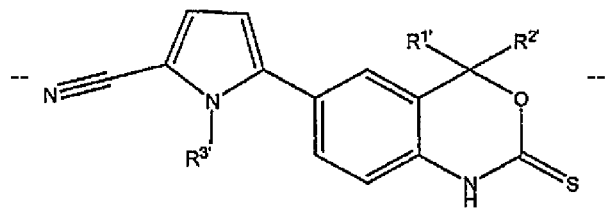

(3)  Scheme II, Col. 14, line 54, replace "NaCO$_3$" with -- Na$_2$CO$_3$ --.
(4)  Scheme VIIa, Col. 19, line 21, replace "R$^8$ or R$^9$ = none" with -- R$_8$ or R$_9$ = none --.
(5)  Col. 22, line 47, replace "contain" with -- containing --.
(6)  Col. 23, line 11, replace "delivery" with -- delivered --.
(7)  Col. 24, line 10, replace "an" with -- a --.
(8)  Claim 1, Col. 34, lines 1-10, replace the following structure:

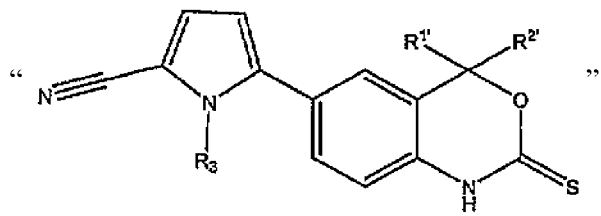

with the following structure:

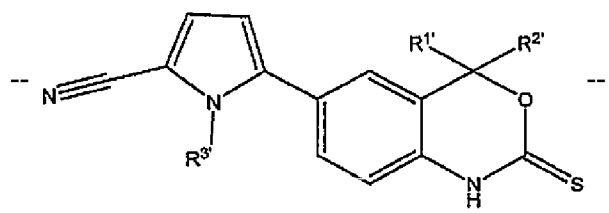

UNITED STATES PATENT AND TRADEMARK OFFICE
CERTIFICATE OF CORRECTION

PATENT NO. : 7,192,956 B2
APPLICATION NO. : 10/601481
DATED : March 20, 2007
INVENTOR(S) : Fensome et al.

It is certified that error appears in the above-identified patent and that said Letters Patent is hereby corrected as shown below:

(9) Claim 10, Col. 35, lines 5-15, replace the following structure:

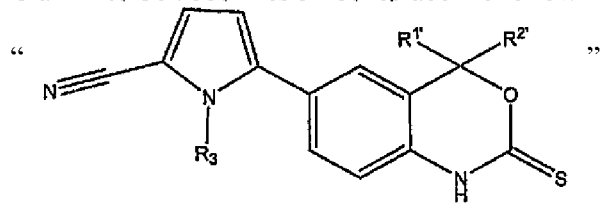

with the following structure:

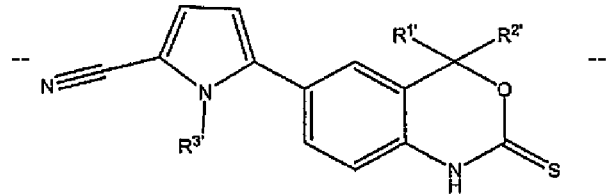

(10) Claim 11, Col. 35, lines 30-40, replace the following structure:

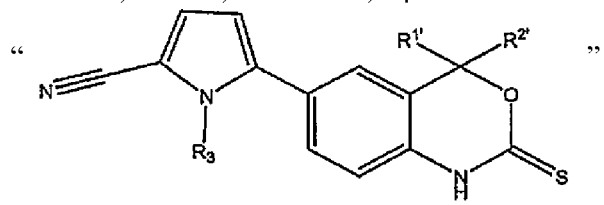

with the following structure:

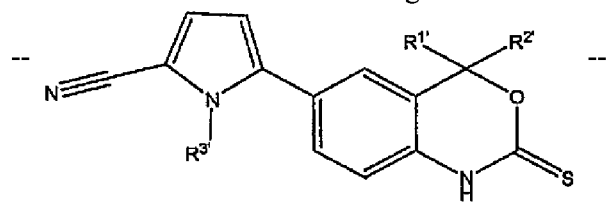

(11) Claim 17, Col. 36, lines 4-12, replace the following structure:

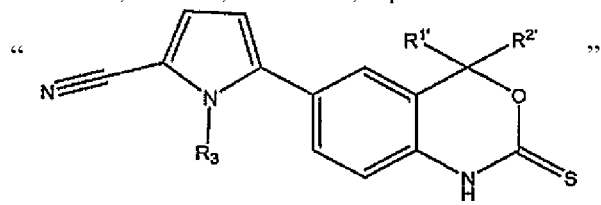

with the following structure:

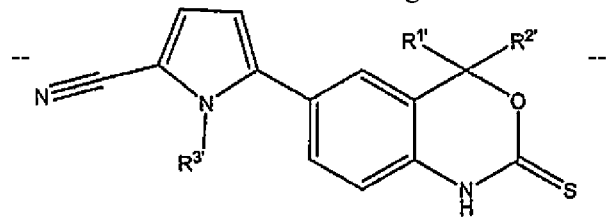

UNITED STATES PATENT AND TRADEMARK OFFICE
CERTIFICATE OF CORRECTION

PATENT NO.      : 7,192,956 B2
APPLICATION NO. : 10/601481
DATED           : March 20, 2007
INVENTOR(S)     : Fensome et al.

It is certified that error appears in the above-identified patent and that said Letters Patent is hereby corrected as shown below:

(12) Claim 19, Col. 38, lines 38-40, replace "H, $C^1$ to $C^6$ alkyl, substituted $C^1$ to $C^6$ alkyl, $C^3$ to $C^8$ cycloalkyl, substituted $C^3$ to $C^8$" with -- H, $C_1$ to $C_6$ alkyl, substituted $C_1$ to $C_6$ alkyl, $C_3$ to $C_8$ cycloalkyl, substituted $C_3$ to $C_8$ --.

(13) Claim 19, Col. 39, lines 1-10, replace the following structure:

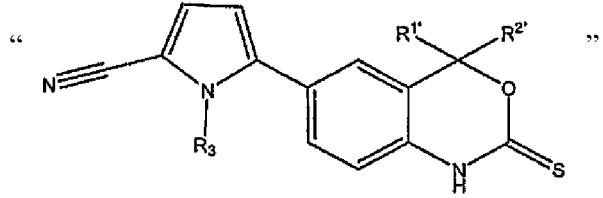

with the following structure:

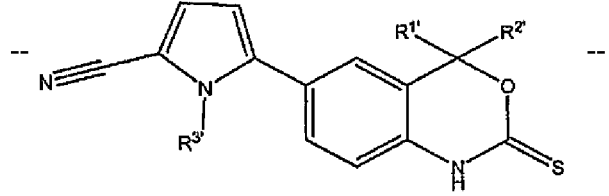

(14) Claim 20, Col. 41, lines 52-60, replace the following structure:

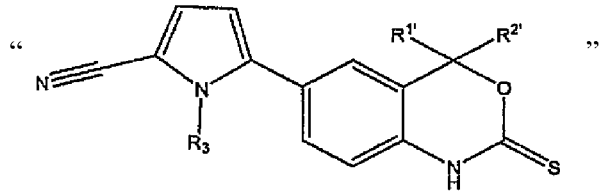

with the following structure:

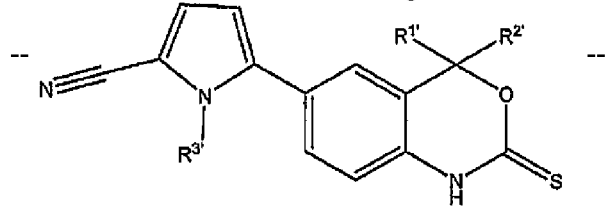

(15) Claim 21, Col. 44, line 16, replace "$CO_2R10$" with -- $CO_2R^{10}$ --.

UNITED STATES PATENT AND TRADEMARK OFFICE
CERTIFICATE OF CORRECTION

PATENT NO. : 7,192,956 B2
APPLICATION NO. : 10/601481
DATED : March 20, 2007
INVENTOR(S) : Fensome et al.

It is certified that error appears in the above-identified patent and that said Letters Patent is hereby corrected as shown below:

(16) Claim 21, Col. 44, lines 22-30, replace the following structure:

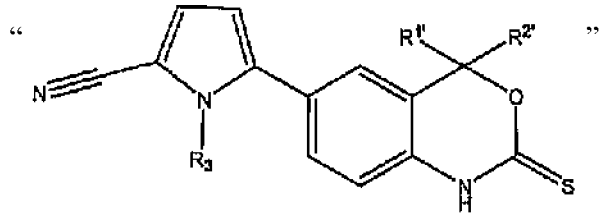

with the following structure:

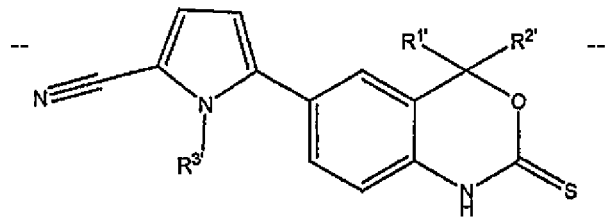

Signed and Sealed this

Tenth Day of July, 2007

JON W. DUDAS
*Director of the United States Patent and Trademark Office*